(12) United States Patent
Dilleen et al.

(10) Patent No.: US 9,063,132 B2
(45) Date of Patent: *Jun. 23, 2015

(54) ASSAY DEVICE AND METHOD

(75) Inventors: John William Dilleen, Alloa (GB);
Phillip Lowe, North Wood (GB); Ruth Polwart, Clackmannan (GB); Jennifer Hay, Glasgow (GB); Claus Marquordt, Edinburgh (GB); Steven Alexander Keatch, Marchmont (GB); Steven Howell, Crieff (GB); Alan Thomson, Dunfermline (GB)

(73) Assignee: INVERNESS MEDICAL SWITZERLAND GMBH, ZUG (CH)

( * ) Notice: Subject to any disclaimer, the term of this patent is extended or adjusted under 35 U.S.C. 154(b) by 904 days.

This patent is subject to a terminal disclaimer.

(21) Appl. No.: 12/753,592

(22) Filed: Apr. 2, 2010

(65) Prior Publication Data

US 2011/0008813 A1 Jan. 13, 2011

Related U.S. Application Data

(63) Continuation of application No. PCT/GB2007/003738, filed on Oct. 2, 2007, which is a continuation-in-part of application No. 12/294,818, filed as application No. PCT/IB2007/001756 on Mar. 29, 2007.

(60) Provisional application No. 60/868,480, filed on Dec. 4, 2006, provisional application No. 60/908,729, filed on Mar. 29, 2007.

(30) Foreign Application Priority Data

Mar. 29, 2006 (GB) .................................. 0606263.2

(51) Int. Cl.
| | | |
|---|---|---|
| *C12Q 1/28* | (2006.01) | |
| *C12Q 1/00* | (2006.01) | |
| *G01N 33/00* | (2006.01) | |
| *G01N 33/53* | (2006.01) | |
| *G01N 33/543* | (2006.01) | |
| *B01L 3/00* | (2006.01) | |
| *G01N 1/00* | (2006.01) | |
| *G01N 27/26* | (2006.01) | |

(52) U.S. Cl.
CPC .... *G01N 33/54326* (2013.01); *B01L 3/502715* (2013.01); *B01L 3/502761* (2013.01); *B01L 3/502769* (2013.01); *B01L 2300/0645* (2013.01); *B01L 2300/0816* (2013.01); *B01L 2300/0887* (2013.01); *B01L 2400/043* (2013.01); *B01L 2400/0688* (2013.01); *G01N 33/54366* (2013.01)

(58) Field of Classification Search
None
See application file for complete search history.

(56) References Cited

U.S. PATENT DOCUMENTS

| | | | |
|---|---|---|---|
| 4,935,147 | A | 6/1990 | Ullman et al. |
| 5,279,936 | A | 1/1994 | Vorpahl |
| 6,695,009 | B2 | 2/2004 | Chien et al. |
| 2002/0079008 | A1 | 6/2002 | Chien et al. |

FOREIGN PATENT DOCUMENTS

| | | |
|---|---|---|
| WO | WO 2007/002579 A | 1/2007 |
| WO | WO 2007/110739 A | 10/2007 |
| WO | WO 2007/110779 A | 10/2007 |

OTHER PUBLICATIONS

Kotz et al. 2005.Optically Addressed Droplet-Based Protein Assay. Journal of American Chemical Society, vol. 127, pp. 5736-5737.*
Wikström et al. 1987. Magnetic Aqueous Two-Phase Separation: A New Technique to Increase Rate of Phase-Separation, Using Dextran-Ferrofluid or Larger Iron Oxide Particles. Analytical Biochemistry, vol. 167, pp. 331-339.*
Morawski et al. 2000. Functional expression of horseradish peroxidase in *Saccharomyces cerevisiae* and *Pichia pastoris*. Protein Engineering .vol. 13, No. 5, pp. 377-384.*
Heinzkill et al. 1998. Characterization of Laccases and Peroxidases from Wood-Rotting Fungi (Family Coprinaceae), Applied and Environmental Microbiology, vol. 64, No. 5, pp. 1601-1606.*

* cited by examiner

*Primary Examiner* — Jon P Weber
*Assistant Examiner* — Kailash C Srivastava
(74) *Attorney, Agent, or Firm* — Steptoe & Johnson LLP

(57) ABSTRACT

An assay method and device can perform at least one (e.g., at least two) assays on a single aliquot of a sample liquid. The device can mix a sample liquid with assay reagents including magnetically susceptible particles. The device is configured to create a sample liquid-air interface with the sample liquid. The magnetically susceptible particles can be located (via an applied magnetic field) at the liquid-air interface when a second liquid contacts the interface to form a liquid-liquid interface. The magnetic particles travel across the liquid:liquid interface to the second liquid. The magnetically susceptible particles are configured to transport an analyte across the interface into the second liquid. An assay for the analyte is performed in the second liquid. An assay for another analyte can also be performed in the sample liquid.

16 Claims, 24 Drawing Sheets

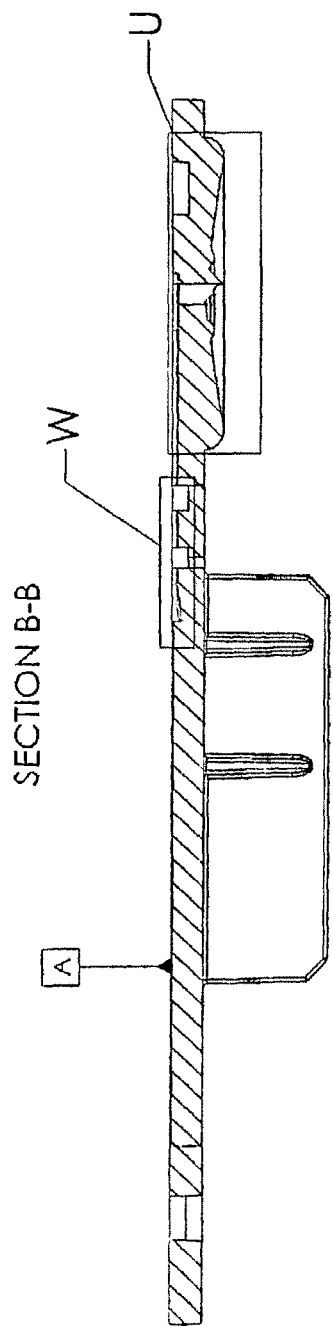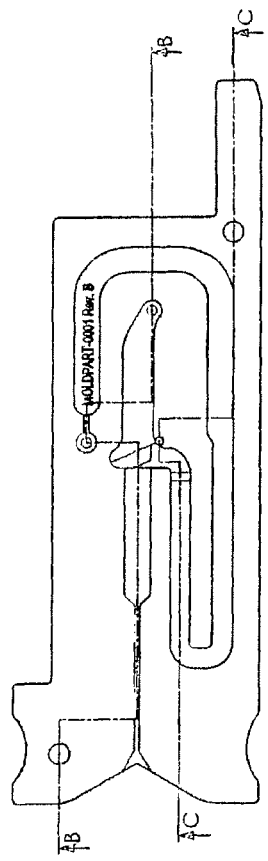
Figure 10A
Figure 10B

ASSAY DEVICE AND METHOD

CROSS REFERENCE TO RELATED APPLICATIONS

This application claims priority under 35 USC 120 to International Application PCT/GB2007/003738, filed Oct. 2, 2007, designating the United States, and is a continuation-in-part of U.S. application Ser. No. 12/294,818 filed Sep. 26, 2008, which is a U.S. national phase of international patent application no. PCT/IB2007/01756 filed Mar. 29, 2007 and claims priority to British provisional application no. GB0606263.2, filed Mar. 29, 2006, to U.S. provisional application No. 60/868,480, filed Dec. 4, 2006, to U.S. provisional application No. 60/908,729, filed Mar. 29, 2007. This application is related to British provisional application no. GB0603049.8, filed Feb. 15, 2006 and to U.S. application Ser. No. 11/013,353 filed Dec. 12, 2004. Each of the foregoing applications is incorporated herein by reference in its entirety.

TECHNICAL FIELD

The present invention relates to assays.

BACKGROUND

Heart failure is a chronic, progressive disease that affects a substantial portion of the world's population. The prevalence and incidence of heart failure is growing due to an aging population and a greater number patients who survive a myocardial infarction.

Clinically, heart failure can be characterized by a syndrome of breathlessness and fatigue, often accompanied by fluid retention, as indicated by an elevated jugular venous pressure and edema. The progression of heart failure is defined in four stages. The term heart failure refers to all of these. Stage A—at risk: patients at high-risk of developing heart failure (patients with coronary heart disease, diabetes, hypertension, and/or valvular heart disease). Stage B—pre-heart failure: patients with structural heart disease but without clinical heart failure symptoms, many of whom have decreased systolic function. Stage C—heart failure: patients who have prior or current symptomatic heart failure due to systolic or diastolic dysfunction and who are responding to therapy. Stage D—advanced heart failure: patients in end-stage or refractory-to-therapy.

Many of the tests and procedures for accurately and successfully diagnosing, managing and treating heart failure are complex, expensive and available only at a hospital or other health-care setting.

SUMMARY

The present invention relates to assays.
In some aspects, the invention relates to a method.
In one aspect a method comprises: (a) introducing a liquid sample to a first portion of a channel of a microfluidic device; (b) contacting, within the microfluidic device, reagent with the liquid sample; (c) contacting, within the microfluidic device, liquid sample with a second liquid wherein the second liquid contains substrate of the reagent; (d) detecting a characteristic of the substrate in the second liquid at a first position in the microfluidic device; (e) contacting the second liquid with reagent at a second position in the microfluidic device and detecting a characteristic of the contacted substrate and/or reagent; (f) contacting reagent from said liquid sample with substrate in the second liquid and detecting a characteristic of the contacted liquid sample reagent and/or substrate; (g) using the characteristics detected in (d) and (e) to validate or adjust the characteristic detected in (f).

In one embodiment detection of a characteristic of the substrate at the first position is in the absence of reagent, i.e. reagent concentration is zero. Preferably, therefore, the second liquid has not contacted reagent.

In other embodiments detection of a characteristic of the substrate at the first position is where the second liquid has contacted a first concentration of reagent. Thus, step (d) can comprise contacting the second liquid with a first concentration of reagent and detecting a characteristic of the contacted substrate and/or reagent at the first position. At the second position substrate in the second liquid can contact a second concentration of reagent wherein the second concentration of reagent is different to the first concentration of reagent.

In some embodiments contacting of the liquid sample with second liquid comprises forming, proximal to a junction between the first portion of the channel and a second portion of the channel, a liquid sample:gas interface; and forming a liquid sample:second liquid interface by flowing a second liquid toward said junction and displacing gas of the liquid sample:gas interface with a second liquid.

In some embodiments detecting a characteristic of the substrate in (d) occurs in the second liquid. Detecting a characteristic of the substrate in (d) can take place prior to formation of the liquid sample:second liquid interface. Detecting a characteristic of the substrate in (d) can occur at a location upstream of said junction with respect to the direction of flow of said second liquid.

In some embodiments detecting a characteristic of the substrate and/or reagent in (e) occurs in the second liquid. Detecting a characteristic of the substrate and/or reagent in (e) can take place after formation of the liquid sample:second liquid interface. Detecting a characteristic of the substrate and/or reagent in (e) can occur at a location downstream of said junction with respect to the direction of flow of said second liquid.

In some embodiments detection of the characteristic of the contacted liquid sample reagent and/or substrate in (f) occurs in the second liquid. Detection of the characteristic of the contacted liquid sample reagent and/or substrate in (f) can take place after formation of the liquid sample:second liquid interface. Detection of the characteristic of the contacted liquid sample reagent and/or substrate in (f) can occur at a location upstream of said junction with respect to the direction of flow of the second liquid. The detection of this characteristic can involve the detection of an assay result at a detection zone in the second channel portion of the microfluidic device.

In some embodiments, the first and second position are in a second channel portion of the microfluidic device, wherein the first position is in a detection zone for detecting an assay result and the second position is in an overflow channel, e.g. at a reagent control zone. The first and second positions are spatially separated in the channel network of the microfluidic device such that following contact with the second liquid mixing, between respective positions, of reagents deposited at or near the respective positions does not occur or is negligible. Reagent can be deposited at the first and/or second positions, or adjacent or proximal to the respective position(s). Detection of the characteristic can occur close to the location of deposited reagent and can be at, adjacent or proximal to, the first and second positions. Sensors can be positioned at the respective positions to detect the characteristic.

In some embodiments the method further comprises the step of comparing a detected characteristic against a reference value. A reference value can be a laboratory standard. It can represent a known activity of the substrate or reagent prior to incorporation in the microfluidic device such that a change in the activity of the substrate or reagent following storage in the microfluidic device can be determined. The comparison step can therefore provide a control for changes in substrate and/or reagent activity.

The detected characteristics of the substrate and reagent at the first and second positions can be used as controls for reagent and/or substrate activity, which are useful to determine whether reagents used in the assay have undergone a change in activity (e.g. reduction in activity) which may affect the assay result. The control values detected can be used to validate the assay result or adjust the assay result to take account of a change in reagent or substrate activity.

Therefore, in some embodiments the method can comprise using the detected characteristics from (d) and (e) to determine a difference in activity of substrate and/or reagent contained in the microfluidic device from a respective reference activity or activities. Determining the difference can involve calculating a difference in activity of substrate and/or reagent contained in the microfluidic device from a respective reference activity or activities. This difference can be used to validate the detected characteristic of the contacted liquid sample reagent and/or substrate, e.g. the assay result. This difference can also be used to adjust a detected characteristic of the contacted liquid sample reagent and/or substrate, e.g. to calculate and apply a correction to the characteristic of the contacted liquid sample reagent and/or substrate. Thus, in some embodiments the initial assay result is corrected to provide an adjusted final assay result.

In some embodiments the step of contacting, within the microfluidic device, reagent with the liquid sample comprises contacting, in the first portion of the channel, reagent and magnetically susceptible particles with the liquid sample, the magnetically susceptible particles forming a complex with the reagent and comprising a binding agent configured to bind an analyte in the liquid sample. The method may further comprise the step of magnetically moving magnetically susceptible particle:reagent complexes across the liquid sample: second liquid interface into the second liquid and to a detection zone in the second channel portion.

The reagent can be, or comprise, one or more enzymes. In some embodiments the reagent is horse radish peroxidase and the substrate is ABTS. The second liquid can also contain hydrogen peroxide.

In one embodiment the method comprises: (a) mobilizing, within a microfluidic device and using a liquid sample, a dry reagent, the liquid sample containing an analyte, (b) subsequently forming, within the microfluidic device, a second liquid-liquid sample interface between a second liquid and the liquid sample, the second liquid comprising a second reagent which is a substrate of the dry reagent; (c) subsequently detecting, at a first position within the microfluidic device, a characteristic of a first amount of the substrate in the second liquid; (d) moving an amount of the mobilized dry reagent and the analyte from the liquid sample into the second liquid to a second position within the microfluidic device, the amount of moved mobilized dry reagent being indicative of the amount of analyte present in the liquid sample; (e) detecting a characteristic of the substrate at the second position; (f) using the characteristics detected in (c) and (e) to validate or adjust the characteristic detected in (e), the validated or adjusted characteristic being indicative of the amount of mobilized dry reagent moved to the second position.

In some embodiments the first amount of substrate is the amount or portion of substrate contained in the second liquid in the region of the reagent control zone and from which the characteristic is detected. The characteristic of the first amount of the substrate can be independent of the amount of analyte present in the liquid sample.

Detection of a characteristic can comprise determination of a characteristic. This may comprise determining, measuring or detecting a signal (quantitatively or qualitatively). The detection can be determining the conversion of one or more substrates into one or more products. In some embodiments detecting a characteristic of the substrate comprises electrochemical detection of oxidized or reduced substrate. This can comprise detection of the oxidation or reduction state of the substrate. In other embodiments it can comprise detection of a fluorescent marker or label.

In one aspect, a method includes transporting a magnetic or magnetically susceptible particle across an interface between a sample reagent mixture and another medium (e.g., a fluid such as a gas or liquid). The particle includes a binder for an analyte or analyte complex. The analyte is determined after transporting the particle and bound analyte across the interface. At least the step of transporting can be performed in a microfluidic device.

In some embodiments, the method includes introducing a liquid sample to a first portion of a channel of a microfluidic device; contacting, within the microfluidic device, magnetically susceptible particles with the liquid sample, the magnetically susceptible particles comprising a binding agent configured to bind an analyte; forming, proximal to a junction between the first portion of the channel and a second portion of the channel, a liquid sample:gas interface; forming a liquid sample:second liquid interface by displacing gas of the liquid sample:gas interface with a second liquid, and magnetically moving the magnetically susceptible particles across the liquid sample:second liquid interface into the second liquid.

The method may be a method for detecting an analyte in the liquid sample, the magnetically susceptible particles adapted to bind the analyte wherein the method further comprises the step of detecting analyte in the second liquid.

The method may be for detecting an analyte and comprise the step of determining an amount of the analyte.

The method may include separating an analyte from the liquid sample and transporting the analyte into the second liquid.

The method may be an in vitro method.

The first and second liquids are typically different. The first liquid may be a bodily fluid from a human or mammal (e.g., blood, serum, or plasma). The second liquid may be a buffer solution.

In some embodiments, the method is an in vitro method for detecting an analyte in a liquid sample of blood, plasma or serum from a human comprising introducing the liquid sample to a first portion of a channel of a microfluidic device; contacting, within the microfluidic device, magnetically susceptible particles with the liquid sample, the magnetically susceptible particles comprising a binding agent configured to bind an analyte; forming, proximal to a junction between the first portion of the channel and a second portion of the channel, a liquid sample:gas interface; forming a liquid sample:second liquid interface by displacing gas of the liquid sample:gas interface with a second liquid, and magnetically moving the magnetically susceptible particles across the liquid sample:second liquid interface into the second liquid.

The method may include determining an assay result. The method may include determining an amount of the analyte. The method may include comparing the amount of analyte determined against a reference amount to produce an assay result. The method may include displaying the determined amount of analyte. The method may include displaying information based on an assay result. The information may be indicative of the assay result (e.g., may be indicative of the amount of analyte in the second liquid). The assay result displayed may be proportional to the amount of analyte in the second liquid.

Forming a liquid sample:second liquid interface by displacing gas of the liquid sample:gas interface with a second liquid may comprise directing the second liquid across the face of the liquid sample at the liquid sample:gas interface.

Forming a liquid sample:second liquid interface by displacing gas of the liquid sample:gas interface with a second liquid may comprise directing a flow of second liquid across the face of the liquid sample at the liquid sample:gas interface to decrease an area of the liquid sample:gas interface. During flow of the second liquid across the face of the liquid sample the first liquid may be held essentially static.

The method may comprise the step of forming a liquid sample:second liquid interface in which substantially no bulk movement of liquid (other than diffusion) occurs across the interface.

The method may comprise the step of magnetically positioning magnetically susceptible particles at a predetermined detection zone in the second channel portion.

The method may comprise magnetically moving the magnetically susceptible particles adjacent or upon a sensor located in, or juxtaposed to, the second channel portion of the device. The particles may be magnetically retained adjacent or upon the sensor for an amount of time sufficient for the sensor to detect a characteristic of the second liquid.

The method may include magnetically positioning the magnetically susceptible particles adjacent one or more electrodes configured in the second channel portion to contact the second liquid. The method may include detecting a characteristic of the second liquid at the electrode(s). The step of detecting a characteristic may comprise detecting an electrochemical signal in the second liquid. The magnetically susceptible particles may be held adjacent or upon the one or more electrodes for an amount of time sufficient for the electrodes to detect an electrochemical signal in the second liquid. The detection may comprise detecting the presence of analyte in the second liquid. The detection may comprise detecting an amount of analyte in the second liquid.

The step of introducing the liquid sample may comprise depositing a quantity of the liquid sample at an inlet of the device, wherein the inlet is in fluid connection with the first channel portion.

The method may be a diagnostic method.

The method may be performed outside of the presence of a medical practitioner.

In some embodiments, the method is a method for detecting NTproBNP in a liquid sample of blood, plasma or serum from a human and the method includes introducing the liquid sample to a first portion of a channel of a microfluidic device; contacting, within the microfluidic device, the liquid sample with reagents comprising magnetically susceptible particles conjugated to a first anti-NTproBNP antibody, and a second anti-NTproBNP antibody conjugated to an enzyme label, to form complexes comprising magnetically susceptible particle, NTproBNP and enzyme label; forming, proximal to a junction between the first portion of the channel and a second portion of the channel, a liquid sample:gas interface; forming a liquid sample:second liquid interface by displacing gas of the liquid sample:gas interface with a second liquid; magnetically moving the magnetically susceptible particles across the liquid sample:second liquid interface into the second liquid; and detecting NTproBNP in the second liquid.

The liquid sample:gas interface may be essentially static with respect to movement along the channel between forming the liquid sample:gas interface and forming the liquid sample:second liquid interface.

In other aspects, the invention relates to a device.

In one aspect a device comprises:

an inlet in fluid connection with a first portion of a channel, the inlet configured to receive a liquid;

a second portion of the channel connected to the first portion at a junction;

wherein the first portion of the channel has a main channel height $h_1$ and a channel height $h'_1$ at the junction, wherein $h_1 > h'_1$ and wherein at the junction, the first channel portion has height $h'_1$ and the second channel portion has height $h_2$, wherein $h_2 > h'_1 > h'_1$.

magnetically susceptible particles disposed in the first channel portion;

wherein the device is configured to form, with a liquid received by the inlet, a liquid interface proximal the junction, the device further comprising:

a reservoir containing a quantity of second liquid and configured to deliver second-liquid released from the reservoir into the second channel portion such that the second liquid flows towards the junction, and at least one sensor configured on the second channel portion to detect a signal from the second liquid.

In some embodiments the ratio $h'_1 : h_2$ is at least 1:2.

In some embodiments proximal to the junction one or more of the internal wall(s) of the first channel portion are hydrophobic. Proximal to the junction one or more of the internal wall(s) of the first channel portion can have a hydrophobic patch, a hydrophobic line or a hydrophobic ring extending around the circumference of the first channel portion.

In some embodiments the inlet is partitioned into one or more first compartments in fluid connection with the first channel portion thereby defining a total volume of the first channel portion and first compartments ($V_t$), and one or more second compartments not in fluid connection with the first channel portion.

In some embodiments the second channel portion has a liquid overflow channel portion, said overflow channel portion partitioned into a first overflow channel portion proximal the junction and a second overflow channel portion distal to the junction, wherein the reagent control zone is located in the second overflow channel portion. The main longitudinal axis of at least one of the first and second overflow portions can be substantially parallel to the first channel portion.

In one aspect a device comprises:

an inlet in fluid connection with a first portion of a channel, the inlet configured to receive a liquid;

a second portion of the channel connected to the first portion at a junction;

magnetically susceptible particles disposed in the first channel portion;

wherein the device is configured to form, with a liquid received by the inlet, a liquid interface proximal the junction, the device further comprising:

a reservoir containing a quantity of second liquid and configured to deliver second liquid released from the reservoir into the second channel portion such that the second liquid flows towards the junction, and at least one sensor configured on the second channel portion to detect a signal from the second liquid, wherein the second channel portion has a liquid overflow channel portion, said overflow channel portion partitioned into a first overflow channel portion proximal the junction and a second overflow channel portion distal to the junction, wherein the reagent control zone is located in the second overflow channel portion.

In some embodiments the main longitudinal axis of at least one of the first and second overflow portions can be substantially parallel to the first channel portion.

In some embodiments the first portion of the channel has a main channel height $h_1$ and a channel height $h'_1$ at the junction, wherein $h_1 > h'_1$ and wherein at the junction, the first channel portion has height $h'_1$ and the second channel portion has height $h_2$, wherein $h_2 > h_1 > h'_1$. Proximal to the junction one or more of the internal wall(s) of the first channel portion can be hydrophobic.

The assay method and device can be used in home testing kits for analyzing species present in the blood. In particular, the device and method facilitate the performance of more than one assay on a small sample volume, and are suitable for use with home testing kits that use the "finger stick" or "finger prick" procedure.

The assay device and method can accept small fluid samples in a simple step, and is able to present small fluid samples for immediate testing in a reliable and reproducible fashion. The present invention provides an efficient way to utilise obtained blood samples in a home testing kit by allowing the performance of a series of tests on the same sample.

Finally, the device and method of the present invention facilitate the execution of more than one assay on the same blood sample by separating and isolating analytes of interest, within a complex mixture. This enables the visualisation of the analytes by a detection procedure. In particular, the present invention affords the use a specific reagent for visualising a marker related to an analyte and the reliable quantification of its presence to inform on a disease state in a subject.

Embodiments permit determination of one or several analytes, such as analytes indicative of disease states in a subject, to be detected.

The invention includes the combination of the described aspects and features except where such a combination is clearly impermissible or expressly excluded.

All documents mentioned in this text are incorporated herein by reference.

BRIEF DESCRIPTION OF THE DRAWINGS

FIG. 10A shows a cross-section through the assay device along line B-B, shown in FIG. 10B.

DETAILED DESCRIPTION

Figure 1:
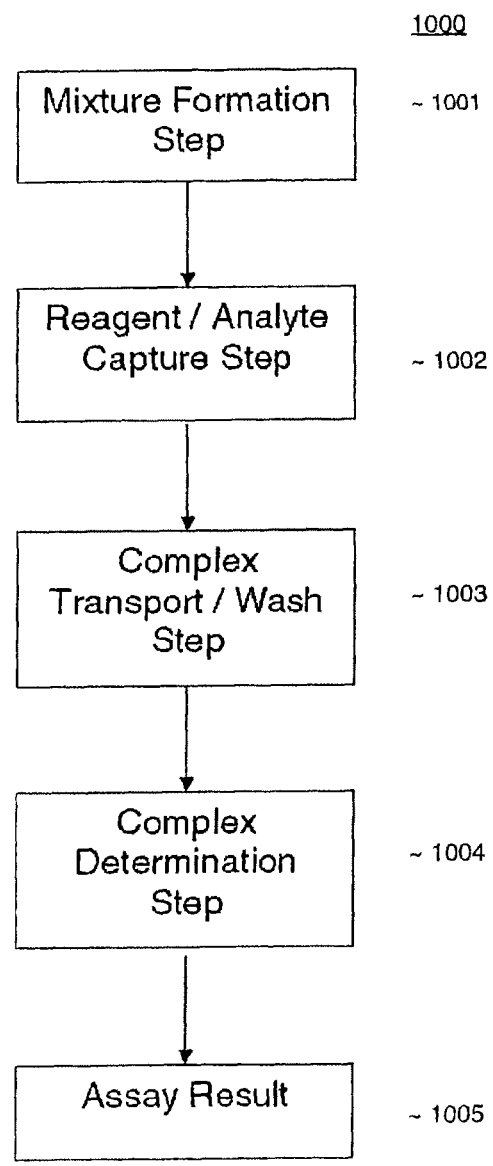
FIG. 1 is a flow chart of an assay method.

Assays for determining (e.g. quantitatively or qualitatively) one or more analytes or indicators in sample material (e.g., a biological sample) are described. Typical analytes are biomarkers related to (e.g., indicative of) the presence of a physiological condition in a mammalian subject. The presence of the physiological condition can be determined based at least in part on the result of the determination of the biomarker (e.g., by comparing the result to a reference value).

The assays can be for use in reaching a diagnosis or prognosis. Assay methods can comprise methods of diagnosis or prognosis of a pathological condition or disease state in a user or susceptibility of the user to a pathological condition or disease state. The assay device can be provided for use in a method of diagnosis or prognosis of a pathological condition or disease state in a user or susceptibility of a user to a pathological condition or disease state. In exemplary embodiments the assay method is an in vitro method not practised on the human or animal body. In exemplary embodiments the assay method is practised on a liquid sample which may be a sample collected from the human or animal body, e.g. a bodily fluid sample such as a human blood sample. In exemplary embodiments the sample is used to conduct the assay and is then discarded, and is not returned to the human or animal from which it was collected.

In exemplary embodiments, magnetically susceptible particles are used in the capture of an analyte, the separation of an analyte from a liquid sample, and in the positioning of the analyte proximal a detection zone.

In some embodiments, an analyte is separated from a liquid sample. After being separated, the analyte is detected in a second medium (e.g., another fluid (e.g., a gas such as air, a different liquid such as a buffer) or flowable medium (e.g., a gel, such as an electrophoresis gel). An exemplary method includes combining magnetically susceptible particles adapted to bind the analyte with the liquid sample to form complexes of magnetically susceptible particle bound analyte. The complexes are magnetically separated from the liquid sample into the second medium.

Separation of the complexes from the liquid sample into the second medium (e.g., another fluid (e.g., a gas such as air, a different liquid such as a buffer) or flowable medium (e.g., a gel, such as an electrophoresis gel)) is typically achieved by a method that includes forming an interface between the liquid sample and second medium. In embodiments, the interface is stable, and essentially static (i.e. diffusion may occur with respect to the interface but the position of the interface is essentially constant). For example, in embodiments in which the interface is performed within a microfluidic device, the position of the interface relative to the microfluidic device may be essentially constant (e.g., the relative position may change by about 5 mm or less, about 2.5 mm or less, about 1 mm or less) at least prior to the transport of the magnetically susceptible particles across the interface as described below. Typically, bulk movement of at least one (e.g., both) of the liquid sample and second medium does not occur with respect to the interface at least prior to the transport of the particles across the interface. In an exemplary embodiment, the position of the interface is essentially constant at least prior to determination of the analyte.

The interface is typically substantially free of gas bubbles. For example, it can be free of gas bubbles or may contain a small number of gas bubbles that do not prevent transfer across the interface of substantially all of the magnetically susceptible particles clustered in the liquid sample adjacent the interface, wherein substantially all of the magnetically susceptible particles is at least about 70% (e.g. at least about 80%, at least about 85%, at least about 90%, at least about 95%, at least about 98%) of the clustered magnetically susceptible particles.

In exemplary embodiments, the interface is formed between the liquid sample and the second medium (e.g., another fluid (e.g., a gas such as air, a different liquid such as a buffer) or flowable medium (e.g., a gel, such as an electrophoresis gel)). In exemplary embodiments the interface is defined by the contacting parts of the liquid sample and the second medium.

A magnetic field is applied to the magnetically susceptible particle:analyte complexes in the liquid sample and the complexes are magnetically moved towards the liquid sample: second medium interface. The magnetic field moves the complexes across the interface and into the second medium. The transport across the interface separates the complexes from the liquid sample.

In exemplary embodiments movement of substantially all of the magnetically susceptible particle:analyte complexes across the liquid sample:liquid interface is optimized by controlling the speed of movement of the magnetic field towards the interface, and across the interface. The timing of movement of the magnetically susceptible particle:analyte complexes across the interface can be controlled to be coincident with, or very shortly after, formation of the liquid sample: second liquid interface.

Having separated the complexes from the liquid sample, the complexes can be further magnetically moved to a sensor (e.g., an electrochemical sensor including one or more electrodes), where the presence of analyte can be detected directly or indirectly.

In exemplary embodiments an indirect detection is performed wherein the complexes include an enzyme label capable of producing a detectable reaction in the presence of one or more enzyme substrates and/or cofactors. For example, the enzyme may produce a product such as an oxidized or reduced enzyme substrate, cofactor or byproduct. The product can be detected electrochemically using the electrochemical sensor. For example, the electrochemical sensor may include one or more electrodes in contact with the second medium.

In exemplary embodiments, the separation of analyte from the liquid sample is desirable as the presence of analyte can then be detected without interference from contaminants (e.g., molecular components such as biological compounds) of the liquid sample. For example, some liquid samples (e.g. blood) produce a non-negligible background electrochemical signal which can interfere with electrochemical determination of certain analytes. Hence separation of analyte from blood may be desirable in order to accurately determine the presence of the analyte.

A device is provided to perform the method of detecting an analyte. The method of detection is an assay for the presence of analyte in the liquid sample and the device an assay device for that method.

The assay device is a microfluidic device having a channel network. The network comprises an inlet connected to a first channel portion, which is connected to a second channel portion at a junction (e.g., a capillary stop) at an intermediate position in the channel network. At the junction the second channel portion can have a cross-sectional area that is larger than the first channel portion creating a capillary stop pressure ($p_{capstop}$) and forming the capillary stop. The capillary stop can alternatively be formed by other means, such as the use of a hydrophobic patch disposed on one or more interior surfaces of the channel.

Liquid sample deposited at the inlet can flow into the first channel portion and fill the first channel portion up to the junction. Liquid sample forms an interface (e.g., a liquid sample:second medium interface) proximal to the junction of the first and second channel portions. The second medium is typically another fluid (e.g., a gas such as air, a different liquid such as a buffer) or flowable medium (e.g., a gel, such as an electrophoresis gel). In embodiments, the second medium is a gas and the interface is a liquid sample-gas interface (e.g., a meniscus).

In some embodiments, the interface is formed by contacting a first interface between (a) one of the liquid sample and the second medium and (b) third medium with the other of the liquid sample and the second medium such that the other of the liquid sample and the second medium displaces the third medium from the first interface. In some embodiments, the third medium is a second liquid (e.g., a buffer) and the device further includes, or is configured to cooperate with, a reservoir of second liquid from which second liquid can be released into the second channel portion to flow towards the junction (e.g., towards the interface). For example, in embodiments where the interface is a liquid sample-gas interface, the second channel portion directs released second liquid to the liquid sample:gas interface to displace the gas (e.g., air) and form a liquid sample:second liquid interface.

In exemplary embodiments the region of the second channel portion adjacent the junction is configured to direct second liquid transversely across a face of the liquid sample:air interface to progressively decrease the area of the liquid sample:air interface as the second liquid flows across the face of the liquid sample:air interface. Subsequent to forming the liquid sample:second liquid interface, the interface may be essentially static and/or bulk movement of liquid relative to the interface may be absent at least until transport across the interface as described above.

The configuration of the second channel portion adjacent the interface can include a change in height and/or width of the second channel portion. In exemplary embodiments the configuration of the second channel portion adjacent the interface includes a tapering of the width and height of the second channel portion to increase the second channel portion width and height at the junction. The second channel portion can further include a change of direction proximal to the junction provided by a bend portion in the second channel portion adjacent the junction. An inside wall of the bend portion can further comprise a capillary stop (e.g. a notch or vent in the inside wall and/or a hydrophobic patch), whilst an outside wall of the bend does not have a corresponding capillary stop. Second liquid advancing towards the junction is retarded at the capillary stop on the inside wall of the bend such that the second liquid advances more rapidly around the outside wall of the bend, in which the junction of the first and second channel portions can be located (at least partially). Typically, the portion of second liquid adjacent the outside wall pivots with respect to the capillary stop. This directs the flow of second liquid transversely across the face of the liquid sample:air interface formed at the junction and facilitates formation of a liquid sample:second liquid interface that is substantially free of air bubbles.

Reagents in the first channel portion form magnetically susceptible particle:analyte complexes with analyte in the liquid sample. These complexes can now be magnetically moved across the liquid sample:second liquid interface and towards a sensor, e.g. one or more electrodes, in the second channel portion where the presence of the analyte can be detected.

The device is configured for operation in conjunction with a meter or reader into which the device is inserted. The meter includes a magnet, which may be an electromagnet, for magnetically moving the magnetically susceptible particles and complexes. The meter also includes components configured to receive signals from the assay device, and a processor and display for determining and displaying an assay result.

The device can be configured to detect more than one analyte.

Assays for determining (e.g. quantitatively or qualitatively) one or more analytes or indicators in sample material (e.g., a biological sample) are described. Typical analytes are biomarkers related to (e.g., indicative of) the presence of a physiological condition in a mammalian subject. The presence of the physiological condition is determined based at least in part on the result of the determination of the biomarker (e.g., by comparing the result to a reference value). Determination of an analyte can be direct or indirect. For example, the presence of an analyte can be indirectly determined by detecting a signal (e.g., an electrochemical or optical signal) resulting from a detectable label (e.g., an enzyme label) conjugated to the analyte. An analyte can be directly determined by, for example, detecting a signal (e.g., an electrochemical or optical signal) resulting from the analyte itself.

Any of the devices or methods described herein can be further configured or implemented to perform at least one action at least in part based on and/or using a result of the determination. For example, the at least one action can be selected from the group consisting of storing the result, making the result available for further processing, displaying the at least one result, recording the result, transmitting the result to a remote location, comparing the result to a reference value, displaying information related to the result, choosing from among multiple actions based on the result, or combination thereof. Here, the term "result" includes values or indicia indicative of the result.

For example, an assay may result in the detection or determination of a characteristic or the detection of an analyte. The result of the determination or detection may be further stored, and/or processed and/or recorded and/or transmitted to a remote location and/or compared to a reference value (e.g. a standard subject population reference value or an individual subject reference value (e.g., a baseline determined from one or more prior determinations of the analyte from the patient)) and/or displayed as an assay result (e.g. to a user of the apparatus) and/or acted on (e.g. through the alteration of a therapeutic programme or strategy). Transmission of a determination or detection to a remote location can be carried out by a communications network, e.g. LAN, WAN, and may be via the internet. Transmission can be wireless transmission to a server, host or proxy. Wireless transmission can be implemented using the Bluetooth® transmission protocol.

The analyte may be any analyte, and more particularly any analyte to which a binding agent, such as an antibody, may be raised and coupled to a magnetically susceptible particle.

In exemplary embodiments an analyte is a natriuretic peptide such as at least one of BNP or NT-proBNP. NT-proBNP (N-terminal truncated pro-brain natriuretic peptide) is the amino-terminal fragment of BNP (brain natriuretic peptide or B-type natriuretic peptide). BNP is the 32 amino acid (aa) peptide cardiac hormone synthesized by ventricular cells and stored as a 108aa pro-peptide. It is secreted in response to ventricular expansion or pressure overload. The pro-peptide is cleaved to release the 32aa active BNP and a 76aa N-terminal fragment (NT-proBNP). BNP and NT-proBNP are markers of ventricular distension and overload. NT-proBNP is correlated with ambulatory cardiac filling pressures in out-patients with chronic heart failure (Braunschweig et al., European Journal of Heart Failure 8 (2006) 797-803) and is indicated as a biomarker of myocardial stretch and chronic heart failure (Murdoch et al., Am Heart J 138(6):1126-1132, 1999) and as a predictor of mortality in acute heart failure (Sakhuja et al., Clinical Chemistry 53:3 412-420 (2007).

Exemplary assays for determining a concentration or amount (qualitative or quantitative) of NT-proBNP in a human blood sample can therefore be used in the monitoring, diagnosis, prognosis, assessment of risk of, and/or assessment of susceptibility to a pathological condition or disease wherein, for example, the pathological condition or disease is chosen from a cardiac condition or disease; heart failure; chronic heart failure; congestive heart failure; myocardial infarction; hypertension.

In other exemplary embodiments the analyte can be chosen from potassium ion, cystatin C, troponin T, troponin I, myeloperoxidase, creatine kinase MB.

The analyte can be a biomarker for a condition that afflicts the mammalian body. The term "biomarker" refers to a biochemical in the body that has a particular molecular trait to make it useful for diagnosing a condition, disorder, or disease and for measuring or indicating the effects or progress of a condition, disorder, or disease. For example, common biomarkers found in a person's bodily fluids (i.e., breath or blood), and the respective diagnostic conditions of the person providing such biomarkers include, but are not limited to, ischemia modified albumin "IMA" (source: lack of oxygen to the blood; diagnosis: coronary artery disease), N-terminal truncated pro-brain natriuretic peptide "NT pro-BNP" (source: stretching of myocytes; exemplary diagnosis related to congestive heart failure), acetaldehyde (source: ethanol; diagnosis: intoxication), acetone (source: acetoacetate; diagnosis: diet; ketogenic/diabetes), ammonia (source: deamination of amino acids; diagnosis: uremia and liver disease), CO (carbon monoxide) (source: $CH_2Cl_2$, elevated % COH; diagnosis: indoor air pollution), chloroform (source: halogenated compounds), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), and $Me_2S$ (source: infection; diagnosis: trench mouth). The biomarker can be a marker of heart failure (e.g. chronic heart failure, heart disease or susceptibility to myocardial infarction (MI), e.g. a marker of MI risk) or a renal marker, e.g. a marker of glomerular filtration rate, which may provide information on blood volume.

In exemplary embodiments the sample material is a liquid such as a biological liquid (e.g., blood, blood plasma, serum, urine, saliva, mucous, tears, semen, cerebrospinal fluid (CSF), lymph or other bodily fluid). In exemplary embodiments the sample material is a bodily fluid from a mammal (e.g. a human who may be male or female). In exemplary embodiments the sample material is whole blood from a human. The analyte can be any component that is found (or may potentially be found) in the sample, such as, for example, a protein, a peptide, a nucleic acid, a metabolite, a saccharide or polysaccharide, a lipid, a drug or drug metabolite, or other component. The assay device can optionally be supplied with a blood separation membrane arranged between a sample inlet and the detection zone, such that when whole blood is available as a sample, only blood plasma reaches the detection zone.

Magnetically susceptible particles can include magnetic particles or particles that can be manipulated (e.g., moved) and/or positioned by a magnetic field. The magnetically susceptible particles can be non-magnetic but susceptible to manipulation or positioning by a magnetic field or be magnetic (e.g. a source of a magnetic field lines). The magnetically susceptible particles can be spherical beads and can have a diameter of at least about 0.05 microns, at least about 1 micron, at least about 2.5 microns, and typically less than about 20 μm. A magnetically susceptible particle can be, for example, a magnetic particle described, in U.S. Patent Application Publication Nos. 20050147963 or 20050100930, or U.S. Pat. No. 5,348,876, each of which is incorporated by reference in its entirety, or commercially available beads, for example, those produced by Dynal AS (Invitrogen Corporation, Carlsbad, Calif. USA) under the trade name DYNABEADS™ and/or MYONE™. In particular, antibodies linked to magnetic particles are described in, for example, United States Patent Application Nos. 20050149169, 20050148096, 20050142549, 20050074748, 20050148096, 20050106652, and 20050100930, and U.S. Pat. No. 5,348,876, each of which is incorporated by reference in its entirety. The magnetically susceptible particles may be ferrous particles.

The magnetic field to which the particles are susceptible can be applied by a magnet, which can be any kind of magnet including a permanent magnet, temporary magnet, or electromagnet. The magnet can be used as a magnetic source for application of a magnetic field towards magnetically susceptible particles.

In exemplary embodiments components or liquid:gas or liquid:liquid interfaces can be positioned proximal to a physical structure. Proximal positioning refers to positioning close to the physical structure. The positioning can be at, or adjacent, the physical structure.

Exemplary embodiments include a microfluidic device. A microfluidic device can comprise a support in which one or more channels are formed to provide a channel network capable of directing flow, and optionally controlling flow, of liquid through part or all of the network. Typically the channel network will have multiple channel portions. In exemplary embodiments the microfluidic device is configured to perform a desired assay, and can be configured to interact with a meter in order to provide an assay result. The microfluidic device is generally small enough to fit on a laboratory bench, and in exemplary embodiments is small enough to be carried by an individual human user in one or two hands.

In exemplary embodiments, channels and channel portions are generally enclosed spaces defined by surrounding walls. The channel can have any cross-sectional shape (e.g. rectangular, trapezoidal, or circular). Channels can be in fluid communication with the atmosphere external to the microfluidic device by means of apertures (e.g., inlets, outlets or vents) formed in the channel network. Channels or channel portions can be open to the atmosphere for part or all of their length, e.g. by not having an enclosing lid. Channels or channel portions can comprise a capillary, i.e. a channel of small internal diameter capable of holding or transporting liquid by capillary action, wherein capillary action is (at least in part) the effect of surface tension that draws a liquid into or along the channel.

Devices according to embodiments can be for use in performing an assay, e.g. on a blood sample. The user can be a human (male or female). In exemplary embodiments the user can perform the assay in the absence of the presence, or in-person assistance, (verbal or otherwise) of a medical practitioner (e.g. nurse, physician, medical doctor, general practitioner, surgeon or phlebotomist). Accordingly, the assay devices can be configured for use away from the hospital, doctor's office, surgery or other medical establishment and can be used in a domestic environment, such as the home or office, or in any convenient location.

A method and/or device and/or meter can be configured for conduct of an assay and production of an assay result to a user in a total test time of less than about 30 minutes (e.g. less than about 20 minutes, less than about 15 minutes, less than about 10 minutes) and in one embodiment in about 10, 11 or 12 minutes.

In exemplary embodiments one or more sensors can be used to determine a characteristic of a liquid and/or to detect a signal. The signal can be the presence or absence of a component, e.g. analyte or oxidized compound. In preferred exemplary embodiments the sensor is an electrochemical sensor including one or more electrodes and the signal is an electrochemical signal (e.g., a signal formed by the reduction of an oxidized compound at an electrode, or the oxidation of a reduced compound at an electrode), which can be detected and/or measured amperometrically and/or voltametrically at the electrode(s). Other sensors include detectors of radiation (e.g. light, X-ray, γ-ray radiation) and/or optical (e.g., fluorescence, reflectance, or absorbance).

In exemplary embodiments components can be bound or conjugated to one another to form complexes (e.g. a magnetically susceptible particle can be conjugated to a binding agent). Binding or conjugation of components can be direct (e.g. binding of an analyte to an anti-analyte antibody) or indirect (e.g. binding of a magnetically susceptible particle to a binding agent through linkers such as streptavidin and biotin).

In exemplary embodiments binding agents are molecules capable of specifically binding to a selected target with high affinity, having a $K_d$ for the target of about 100 μM or less (e.g. less than about 50 μM, less than about 10 μM, less than about 1 μM, less than about 100 nM, less than about 10 nM, less than about 1 nM, less than about 100 pM, less than about 10 pM). The first and second binding agents can be respectively chosen from an antibody (monoclonal or polyclonal), antibody fragment (e.g. scFV fragment), antibody binding domain, aptamer or other recognition reagent. The first and second binding agents can be different, e.g. an antibody and an aptamer.

In exemplary embodiments reagents are provided in an assay device (e.g., in dry form). The reagents can be configured to participate in an assay, e.g. to detect presence of analyte, and can be configured to form conjugates and/or bind the analyte. In exemplary embodiments, the reagents include conjugates of magnetically susceptible particle and at least one reagent (e.g., an antibody labeled enzyme) configured to bind the analyte and form a ternary complex with the magnetically susceptible particle. In exemplary embodiments conjugates of magnetically susceptible particle and reagents are configured to participate in a sandwich assay involving first and second binding agents to form a ternary complex.

Exemplary embodiments provide a device and method for performing an assay on a single small volume blood sample, or other biological materials or complex mixtures.

Exemplary embodiments will now be described in detail, with reference to the accompanying figures. The invention includes the combination of the features described in the exemplary embodiments except where such a combination is clearly impermissible or expressly avoided.

Referring to FIG. 1 an assay method 1000 includes a mixture formation step 1001, a reagent/analyte capture step 1002, a complex transport step 1003, a complex determination step 1004 and a formation of an assay result step 1005. Typically, method 1000 is performed using an assay device including a reagent zone, in which the sample reacts with the reagents, a detection zone in which determination of the analyte is performed (either qualitatively or quantitatively), and an interface zone, which provides an interface between the reagent zone and the detection zone.

In mixture formation step 1001 a mixture including a quantity of sample material (e.g. a sample liquid such as blood from a human) and reagents capable of binding to an analyte is formed. In an exemplary embodiment the reagent capable of binding to the analyte may be an antibody or antibody domain or fragment (e.g. scFv) capable of binding to the analyte. In reagent/analyte capture step 1002 the reagents capable of binding the analyte form complexes with analyte that is present in the sample. In complex transport step 1003 reagent:analyte complexes formed during the previous step may be washed to remove non-complex material and are transported to a detection zone. In complex determination step 1004, the presence of reagent:analyte complexes that have been transported to the detection zone is determined (e.g. qualitatively or quantitatively). The assay result is formed in step 1005 as a result of the extent of detection of reagent:analyte complexes in the preceding step. For example, detection of reagent:analyte complexes may be indicative of the diagnosis or prognosis (new or continued) of a disease state or pathological condition of a user or patient. Therefore, the detection of reagent:analyte complexes may be used or processed (e.g. by comparison with a reference value), to provide an assay result, which may be displayed to the user.

Assay method 1000 will now be discussed in greater detail.

In mixture formation step 1001 a mixture is formed between reagent materials that are disposed within a reagent zone of an assay device and a quantity of sample material sufficient to fill the reagent zone of the assay device. A sample of blood can be obtained from a finger stick or a venous puncture. The volume of blood is typically about 10 µl or about 5 µl.

Several reagents are present within the reagent zone of the assay device. The reagents typically include the following species; magnetically susceptible particles, a first reagent capable of binding to the analyte, a second reagent capable of binding to the analyte concurrently with the first reagent (e.g., as in a sandwich). Typically, the reagent binds to a first unique region of the analyte and the second reagent binds to a second unique region of the analyte. The first reagent is configured to bind to the magnetically susceptible particles even in the absence of analyte (e.g., in a non-specific binding reaction). For example, the first reagent may include a biotin portion and the particle may be coated with streptavidin, which captures the biotin modified first reagent. The second reagent includes a detectable label (e.g., an enzymatic label such as an enzyme). In an exemplary embodiment, the second reagent is a labeled particle (e.g., a non-magnetically susceptible particle such as a colloidal gold sol particle) that is conjugated with a binding reagent for the analyte (e.g., an antibody for the analyte) and with an enzymatic label. Typically, the particle includes multiple enzymatic labels thus increasing the number of enzyme labels that become part of the reagent:analyte complex. The second antibody-enzyme conjugate is typically provided pre-associated with the labeled particles.

In general, the first and second recognition reagents do not associate with one another in the absence of analyte. The presence of analyte, however, can associate the first and second recognition reagents together, in a ternary complex The second reagent can recognize the same or a different analyte and can be a binding agent that specifically binds the same or a different analyte. The reagent zones can include further reagents such as redox mediators, substrates for particular enzymes and salts suitable for forming buffer solutions. The second binding agent can be linked to a particle that can induce mobility on the so-formed ternary complex. The particle can be, for example, a polymer microsphere, a metal nanoparticle, or a magnetically susceptible particle.

When the reagents are mobilized by a sample liquid including the analyte, the reagents interact with the analyte to form a complex including the magnetically susceptible particle, the first reagent, the analyte, and the second reagent. The streptavidin coated magnetically susceptible particle can accommodate a number of biotin modified reagents capable of binding to the analyte. Accordingly, each complex may include multiple analyte molecules and multiple second reagents.

The reagent zone may include one or more additional reagents such as, for example, an anti-coagulant to inhibit clotting of blood within the reagent zone and/or buffer salts. Buffer salts present in the reagent zone control the pH of the mixture to give a pH value that favours the formation of complexes. The pH value is maintained at a desired pH, for example the pH may be maintained within a range of between about pH 7.2 and about pH 7.6.

Reagent/analyte capture step 1002 includes forming complexes between the reagents and analyte contained within the sample. When a sample is applied to the assay device, the dried reagents initially form an inhomogeneous mixture with the sample. Within a short interval of time, the reagents become sufficiently hydrated that they begin to interact with the sample. The first and second antibodies bind to analyte and form complexes. The biotin labeled first reagent binds to the streptavidin coated magnetically susceptible particle(s). The second reagent (e.g., a non-magnetically susceptible particle conjugated to an enzyme label and a binding agent for the analyte) binds the analyte.

Complex transport/wash step 1003 includes moving the reagent:antibody complexes from the reagent zone to the detection zone. The detection zone is filled (e.g., actively)

with a buffer solution during the course of a sample assay. Buffer is released from a reservoir at a predefined time after sample has been applied to the assay device. Buffer solution fills the detection zone and the interface zone. When buffer solution is delivered into the interface zone, the buffer forms a sample liquid:second liquid interface with the sample in the reagent zone (as will be described in more detail below). Excess buffer solution moves in to an overflow channel. When buffer has made contact with and formed an interface with the sample there is a continuous liquid path through the microfluidic network of the assay device. The reagent:analyte complex can thus be moved along the length of the assay device supported in a continuous liquid stream.

A magnetic field can be used to manipulate the reagent:analyte complex within the assay device. The reagent:analyte complex can be drawn along the reagent zone, through the interface zone to the detection zone by a magnetic field. The path of the magnetic field moves in a direction that transfers magnetically susceptible particle complexes from the reagent zone to the detection zone.

In some embodiments, one or more of the detection zones include one or more electrodes. The electrodes can be formed of a material selected for electrical conductivity and low reactivity with sample components, for example, silver, gold, aluminum, palladium, platinum, iridium, a conductive carbon, a doped tin oxide, stainless steel, or a conductive polymer. The electrodes in the detection zones (the working electrodes), in conjunction with second electrodes in the reference zones (the reference electrodes) can measure an electrical property of the sample, such as a voltage or a current. Alternatively, the detection zones and the reference zones can each have at least one working electrode and counter electrode. That is, the detection and reference zones can make independent measurements. Optionally, counter electrodes are also included in the assay device. Assay devices including electrodes for measuring electrical properties of a sample are described in, for example, U.S. Pat. Nos. 5,708,247, 6,241,862, and 6,733,655, each of which is incorporated by reference in its entirety.

In some embodiments, the assay device base, assay device lid, or both have a translucent or transparent window aligned with the detection zone. An optical change that occurs in the detection zone can be detected through the window. Detection can be done visually (i.e., the change is measured by the user's eye) or measured by an instrument (e.g., a photodiode, photomultiplier, or the like). In general, the reference zone is similar in nature to the detection zone. In other words, when the detection zone includes an electrode, the reference zone can likewise include an electrode. When the detection zone is aligned with a window for optical measurement, the reference zone can similarly be aligned with a window for optical measurement. In some embodiments, the reference zone is not adapted to collect analyte. Alternatively, the reference zone is adapted to collect analyte, but performs a different analysis on said analyte. Thus, the detectable change measured in the reference zone can be considered a background measurement to be accounted for when determining the amount or concentration of analyte present in the sample.

During complex determination step 1004 magnetically susceptible reagent:analyte complexes that have been transferred to the detection zone can be measured. In an exemplary embodiment the detection zone includes electrodes that can be used to perform an electrochemical analysis of the sample. The enzyme labeled second reagent that is part of reagent:analyte complex can convert a substrate present in the buffer used to fill the detection zone. The substrate can be converted from a first form that is not detectable to a second form that is detectable. A measurement electrode within the detection zone can be used to measure the detectable form of the substrate. For example, an amperometric measurement can be made, in which a working electrode is polarised at a certain potential versus a reference electrode e.g. a silver/silver chloride (Ag/AgCl) reference electrode. For example, potassium ferricyanide can be converted (reduced) to potassium ferrocyanide by glucose oxidase during the conversion of glucose to gluconic acid. Any potassium ferrocyanide formed can be measured at about +400 mV vs Ag/AgCl as a positive current. The ferrocyanide is re-oxidised back to ferricyanide by the working electrode. An electroactive species can be oxidised, in which case it loses electrons to the electrode, or reduced, in which case it receives electrons from the electrode. The transfer of electrons between the electrode and the electroactive substance results in a measurable current, which may be a positive or negative current.

An amperometric measurement of an electroactive substance can be used to construct a calibration line. A known amount of substance yields a unique current, which can be described by the equation (Eq. 1) $y=mx+c$, where y represents the measured current, x represents the concentration of substance, m is the gradient of the line and c is the intercept of the line on the y-axis. Thus the measured current can be used to determine the concentration of an unknown amount of substance in solution following rearrangement of Eq. 1 to give (Eq. 2) $x=(y-c)/m$.

The buffer contained within the reservoir of the assay device includes a buffer salt and a substrate for the enzyme. The buffer salt buffers the pH to provide an environment suitable for the enzyme to convert the substrate to a product which can be detected. For example, the buffer salt may be an acetate buffer (e.g., sodium acetate). In some embodiments, the buffer can include at least about 100 mM sodium acetate (e.g., at least about 110 mM sodium acetate). The buffer solution can also contain a chloride salt to stabilise the electrochemistry of the reference electrode during analysis (e.g. potassium chloride (KCl)). In some embodiments the chloride salt can include at least about 100 mM KCl (e.g. at least about 125 mM KCl). The buffer solution can also include a detergent to reduce the likelihood of antibody complexes from adhering to the internal surfaces of microfluidic network 508. In an exemplary embodiment the buffer solution includes 0.1% (v/v) Tween-20™. The buffer also includes substrate(s) for the enzyme label, which in the case of horse radish peroxidase is 2,2'-azino-bis(3-ethylbenzthiazoline-6-sulphonic acid) (ABTS) and hydrogen peroxide ($H_2O_2$). In some embodiments the buffer contains at least about 5 mM ABTS and at least about 5 mM $H_2O_2$.

The enzyme label that is conjugated to second binding agent can be horse radish peroxidase (HRP), for example. HRP catalyses the conversion of hydrogen peroxide and ABTS to water and oxidised-ABTS. Any oxidised-ABTS that is produced can be measured electrochemically at a working electrode. Therefore during complex determination step 1004 any reagent:antibody complexes that have been transported through the microfluidic network of assay device can be measured according to the amount of oxidised-ABTS that is produced in the proximity of a measurement electrode. The measured current is proportional to the amount of oxidised-ABTS according to Eq. 2 and hence the measured current is proportional to the amount of analyte in the complexes that have been transported to the electrode.

In forming an assay result step 1005, the measurement result obtained during complex determination step 1004 is used to determine an assay result. In exemplary embodiments the assay result comprises displaying or communicating a value or signal indicative of the amount or concentration (quantitative or qualitative) of analyte detected in the assay. In exemplary embodiments the assay result comprises determining the status of the user, as regards the analyte. Depending on the analyte under investigation an elevated measurement result can indicate a diagnosis or prognosis for a disease state or pathological condition associated with the analyte.

In forming an assay result step 1005 a user of the assay device can be presented with information. If the user is qualified to make a clinical judgment (such as a medical doctor) the information might be different compared with a non qualified person, such as a user performing a self-test measurement. A health care professional will typically want numerical data that will facilitate a prognosis or provide a diagnosis. An end user will typically want reassurance that "the way they feel" is a consequence of (i) an unrelated issue, e.g. indigestion or (ii) occurrence or re-occurrence of heart failure, in which case they will be prompted to dial 911, for example.

Assay Device

Figure 3:
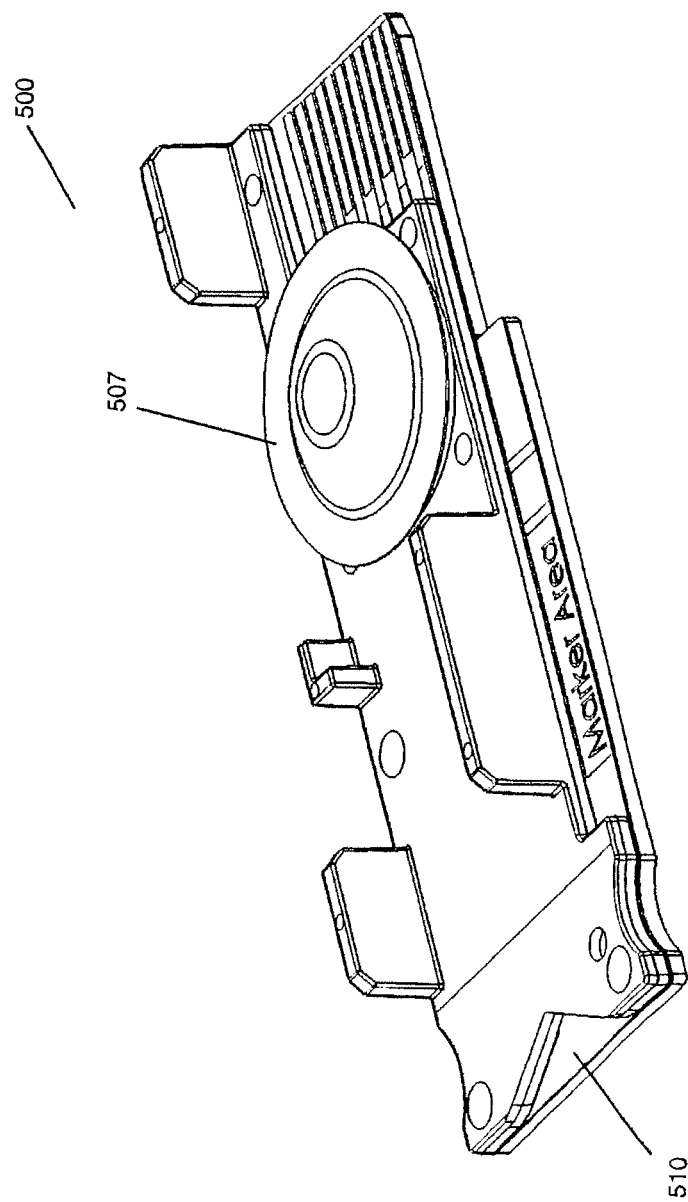
FIG. 3 shows a perspective view of an assay device (including buffer pouch)
Figure 6:
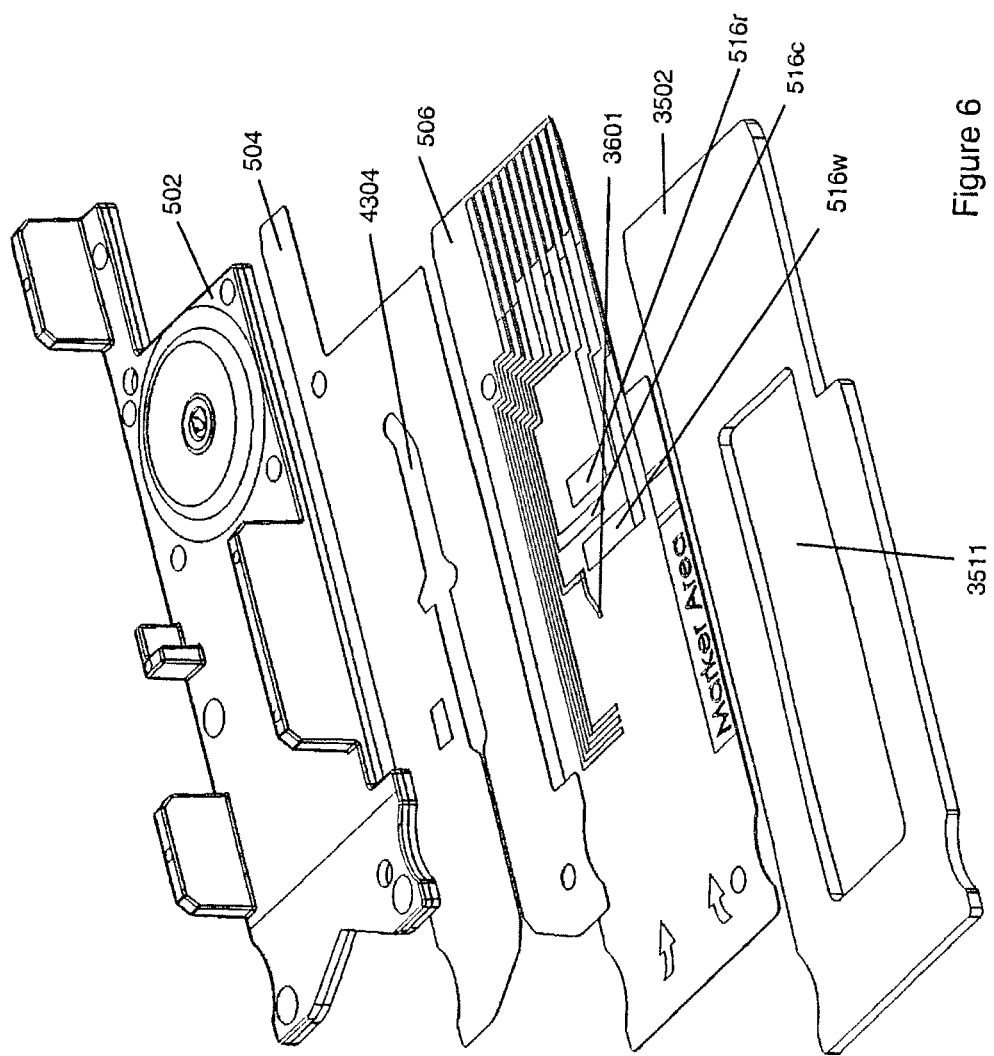
FIG. 6 shows a perspective view from above of the component layers of an assay device.

Referring to FIGS. 3-11, an exemplary embodiment of the assay device is shown. The assembled device is shown in FIG. 3. Referring to FIGS. 3 and 6, the assay device is a microfluidic device in which a channel network is formed. The device has a base 502 that can be formed from a plastics substrate, such as polycarbonate in which the channel network can be formed by techniques well known to persons skilled in the art such as moulding, laser ablation or milling of the substrate (as described above).

The device has a laminate structure (as shown in FIG. 6) being made up of multiple layers. The microfluidic network is defined by a three layer laminate in which a first substrate layer 502 is joined to a third substrate layer 506 by a second substrate layer 504 comprising an adhesive strip, as described above. In an exemplary embodiment a further adhesive strip joins the third substrate layer 506 with a packing piece 3502 to form a device having five laminate layers. The packing piece has a cut-out section 3511 configured to permit a magnet in meter 400 to be positioned in close proximity with the external surface of the third substrate layer 506.

The first substrate layer 502 further comprises a raised annulus 3510 having a liquid inlet 520 proximal its centre and a sharp projection 3506 positioned at or adjacent the inlet. An O-ring seal 2402 is seated on or adjacent the annulus and a liquid containing reservoir 507 is received in the annulus, a wall of which is positioned adjacent the sharp element or projection 3506.

Figure 4:
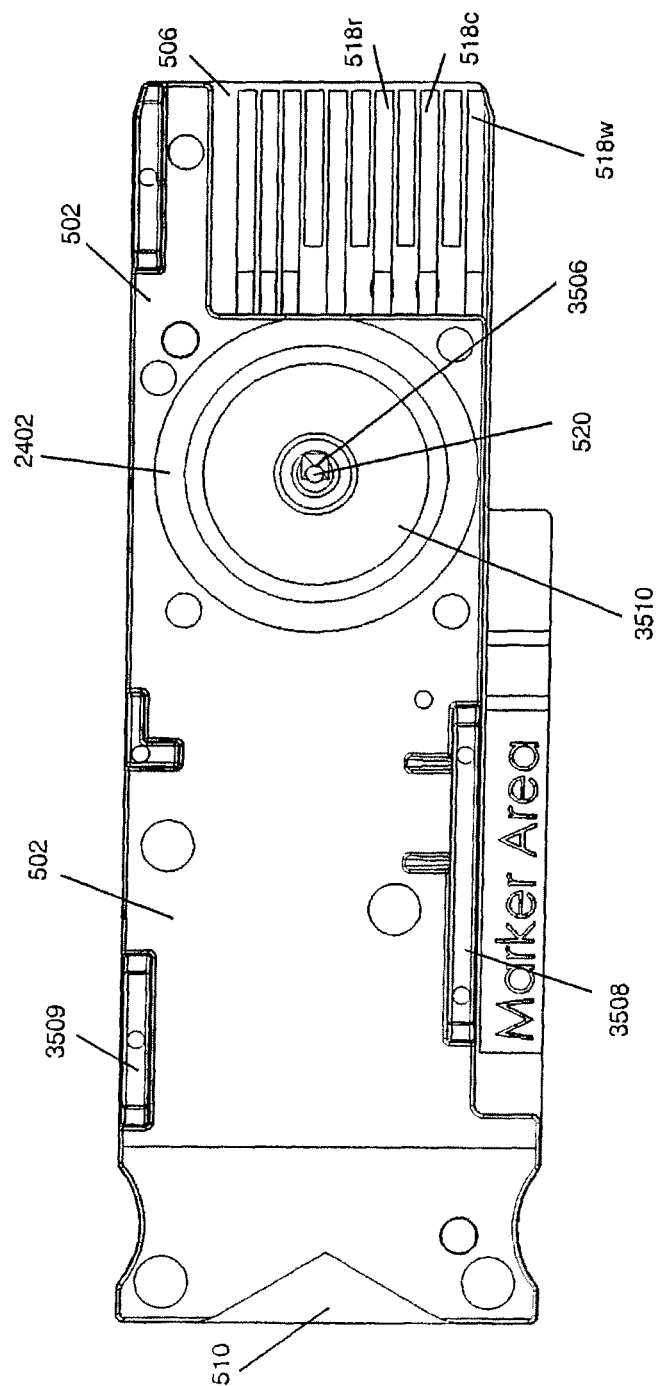
FIG. 4 shows a plan view of an assay device above (excluding buffer pouch)
Figure 5:
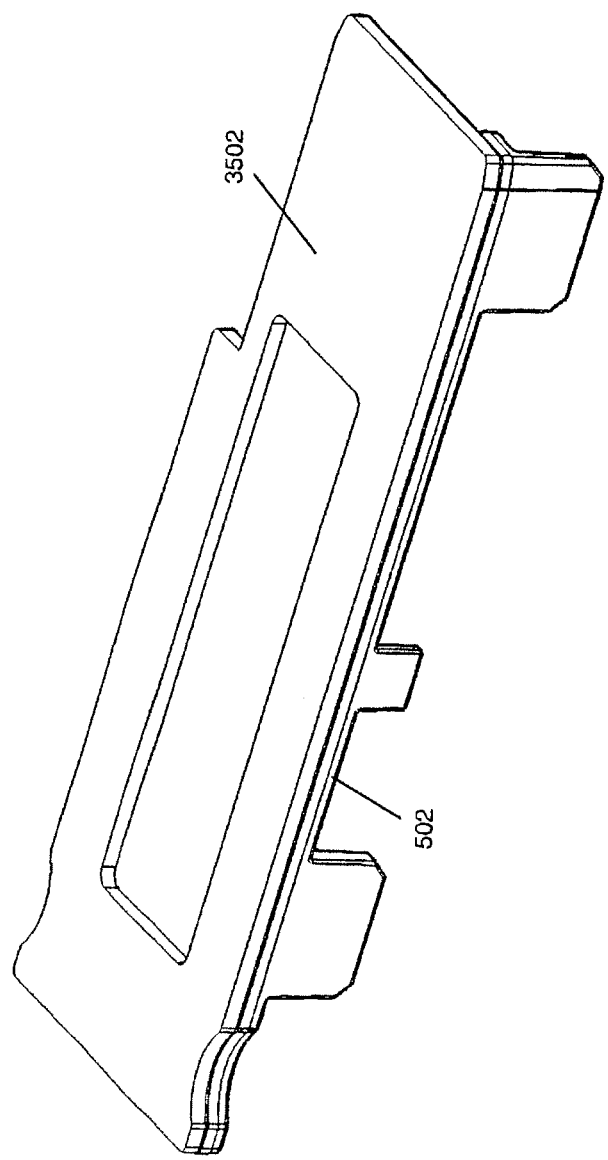
FIG. 5 shows a perspective view of an assay device from underneath.
Figure 10C:
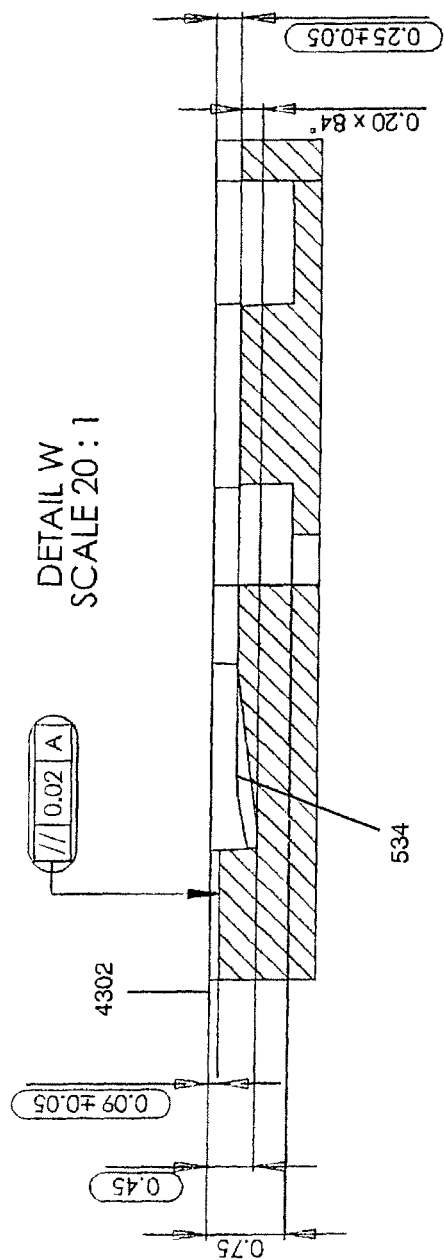
FIG. 10C shows an enlarged view of detail W from FIG. 10A.
Figure 10D:
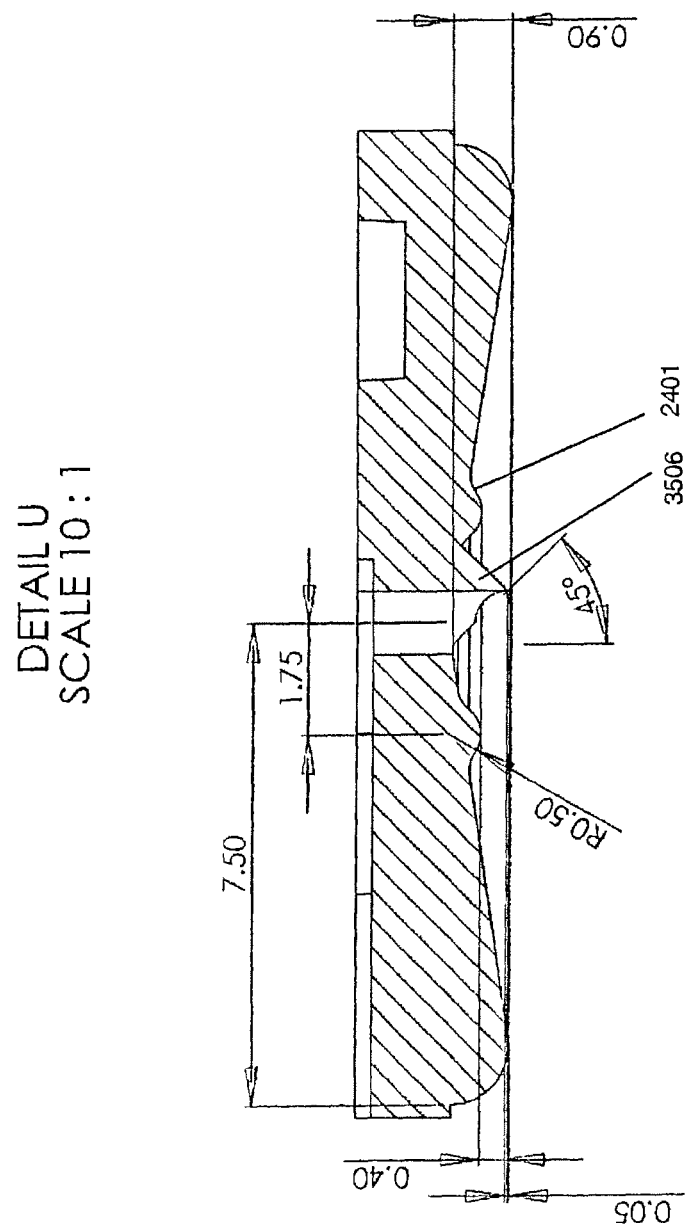
FIG. 10D shows an enlarged view of detail U from FIG. 10A.
Figure 11A:
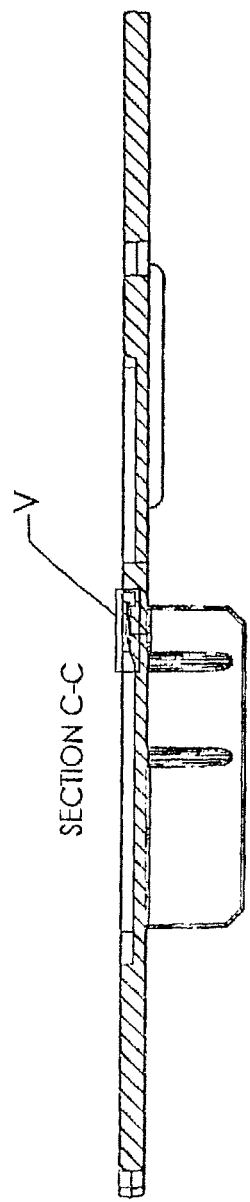
FIG. 11A shows a cross-section through the assay device along line C-C, shown in FIG. 11B.
Figure 11B:
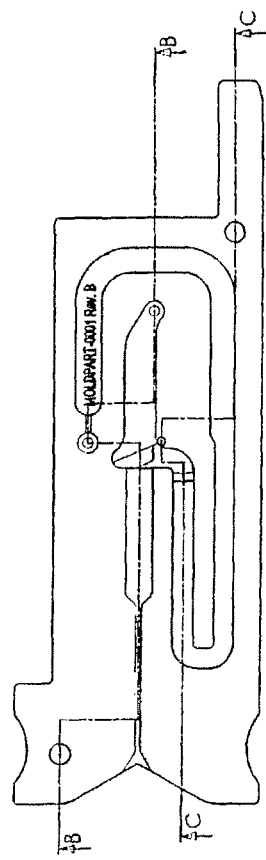
FIG. 11C shows an enlarged view of detail V from FIG. 11A.
Figure 11C:
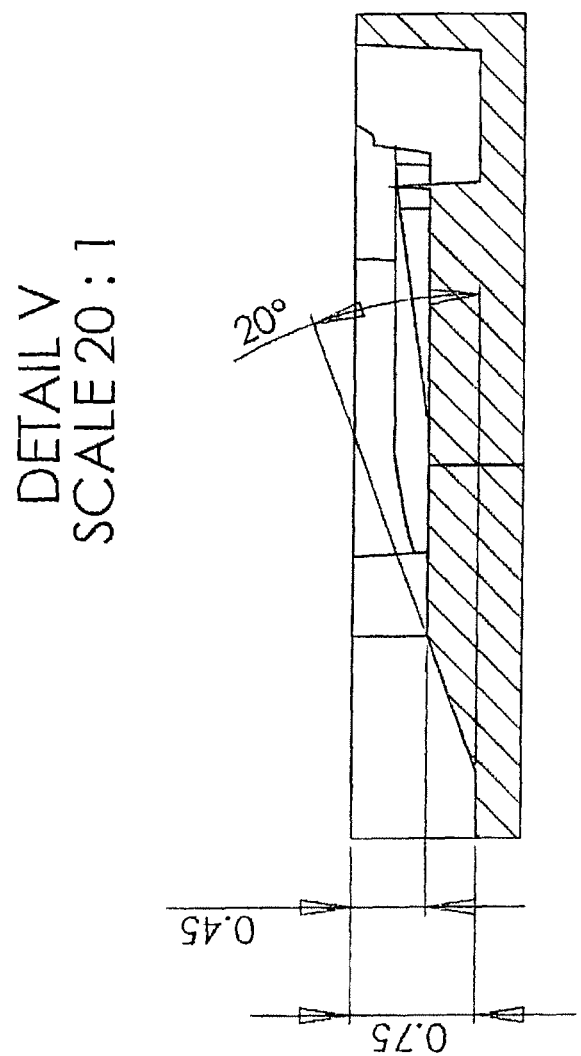

Referring to FIGS. 4 and 10D, the sharp projection 3506 is formed as part of the substrate 502. In an exemplary embodiment the projection 3506 has a pyramid structure the apex of which forms the sharp point 3506 which facilitates puncture of reservoir 507. In an exemplary embodiment the sharp projection is an integral part of substrate 502 and both may be moulded from plastics material. The sharp projection is located adjacent liquid inlet 520, wherein the entrance to liquid inlet 520 is formed by an aperture in one side of the pyramid structure. Projection 3506 projects into the centre of the space defined by the raised annulus 3510 and towards a base wall of the reservoir 507 when received in the annulus. In other embodiments the sharp projection 3506 can be made of metal (e.g. steel) or plastics material.

In exemplary embodiments the reservoir 507 is a pouch having a wall, e.g. a base wall, that may be ruptured by sharp projection 3506 on the assay device 500. In one exemplary embodiment the base wall has a generally smooth outer surface which may be generally planar or convex.

Figure 13:
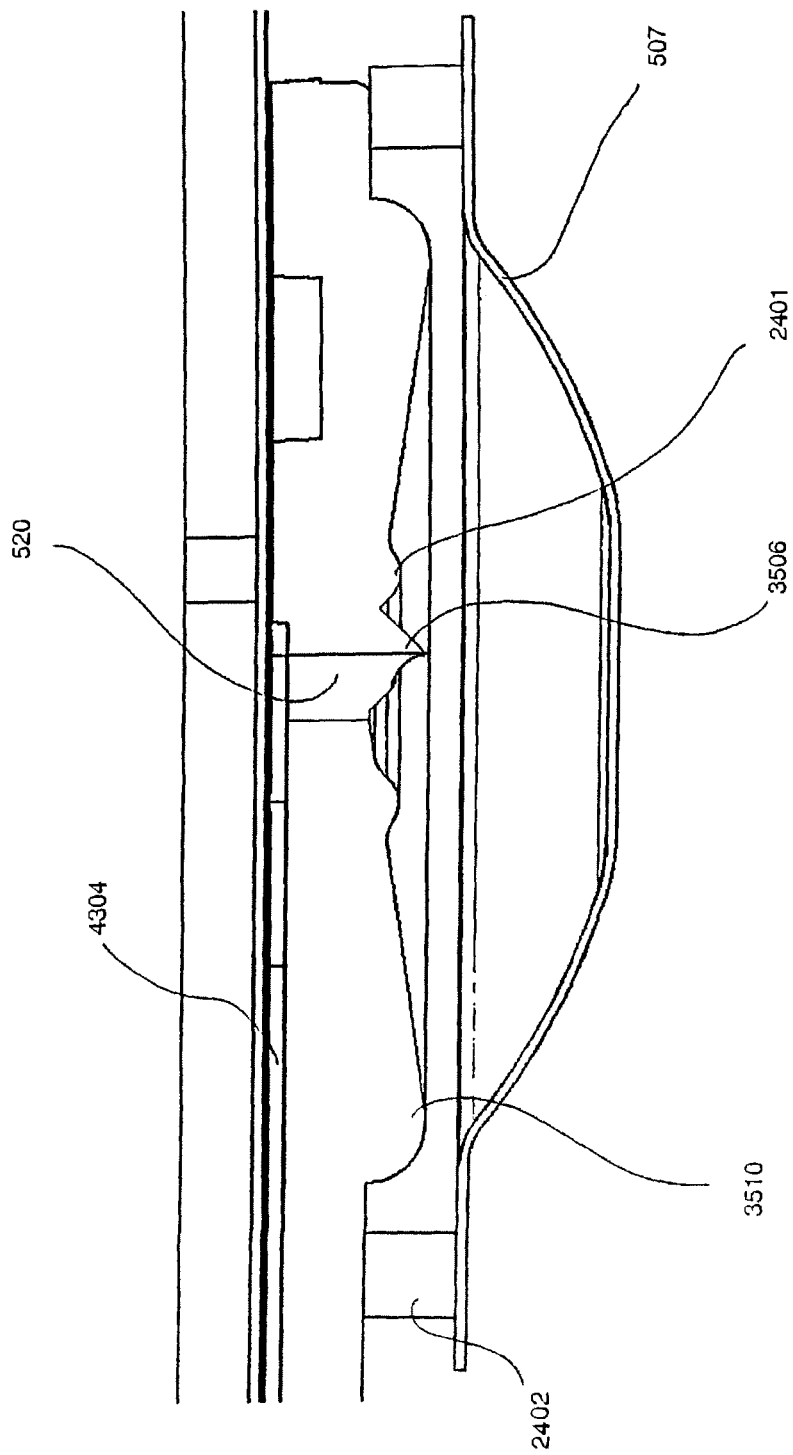
FIG. 13 shows an enlarged view of the interface of the buffer pouch and sharp projection.

Referring to FIG. 13, in an exemplary embodiment a seal or gasket (e.g. an O-ring seal) 2401, e.g. of about 400-600 μm thickness, having an internal diameter sufficient to encompass the sharp projection and inlet 520 (e.g. at least about 1.5 mm, at least about 2 mm, at least about 3 mm, less than about 5 mm, less than about 4 mm) is formed or placed around the sharp projection 3506 such that when the reservoir 507 is compressed against the assay device and toward the sharp projection 3506 a gas-tight seal is formed between the reservoir and the assay device preventing air from entering the assay device via the inlet 520 such that liquid in the second channel portion 4304 is substantially free of air or other gas bubbles.

In an exemplary embodiment seal 2401 is integrally formed with the substrate 502 and is a raised circular ridge encompassing the sharp projection 3506 and liquid inlet 520. In operation, buffer pouch 507 is pushed towards the sharp projection 3506 so as to rupture the buffer pouch and release liquid. The surface of the buffer pouch 507 adjacent the sharp projection is urged against seal 2401 to form an air-tight seal around the sharp-projection 3506. The liquid forced from buffer pouch 507 and entering inlet 520 is therefore substantially free of air, or gas bubbles. Accordingly, a slug of liquid is forced into second channel portion 4304 and towards the junction 4305. The absence of air, or large gas bubbles, in the slug of liquid helps form a stable liquid:liquid interface at junction 4305 and provides for high performance electrochemical detection at the working electrode.

In some exemplary embodiments the reservoir 507 is made from plastics and/or metal foil material and sealed to form a pouch, bag or sachet containing liquid, e.g. buffer liquid. The reservoir 507 can be made from first and second materials, wherein one of the materials is softer and/or thinner than the other, the softer or thinner material forming at least part of the wall that is configured for rupture by the sharp projection 3506 on the assay device 500. In one exemplary embodiment the reservoir 507 has a volume of about 40 μl (e.g. at least about 50 μl, at least about 60 μl, less than about 100 μl).

In one exemplary embodiment the reservoir 507 is made from a first material (e.g. plastics material) and a second material (e.g. metal foil such as aluminium foil). The reservoir is dome-shaped having an upper convex part formed by the first material and a lower planar part made from the second material and forming the base of the dome. The planar part is thin (e.g. at least about 20 μm thickness) and can be punctured when forced towards the sharp projection. The lower planar part is positioned adjacent the sharp projection. Application of force to the upper convex part forces the lower planar part and sharp projection together, rupturing the reservoir and releasing fluid into inlet 520. The lower planar part is pushed against the seal located around the sharp projection and inlet to prevent air mixing with fluid entering inlet 520.

Figure 7:
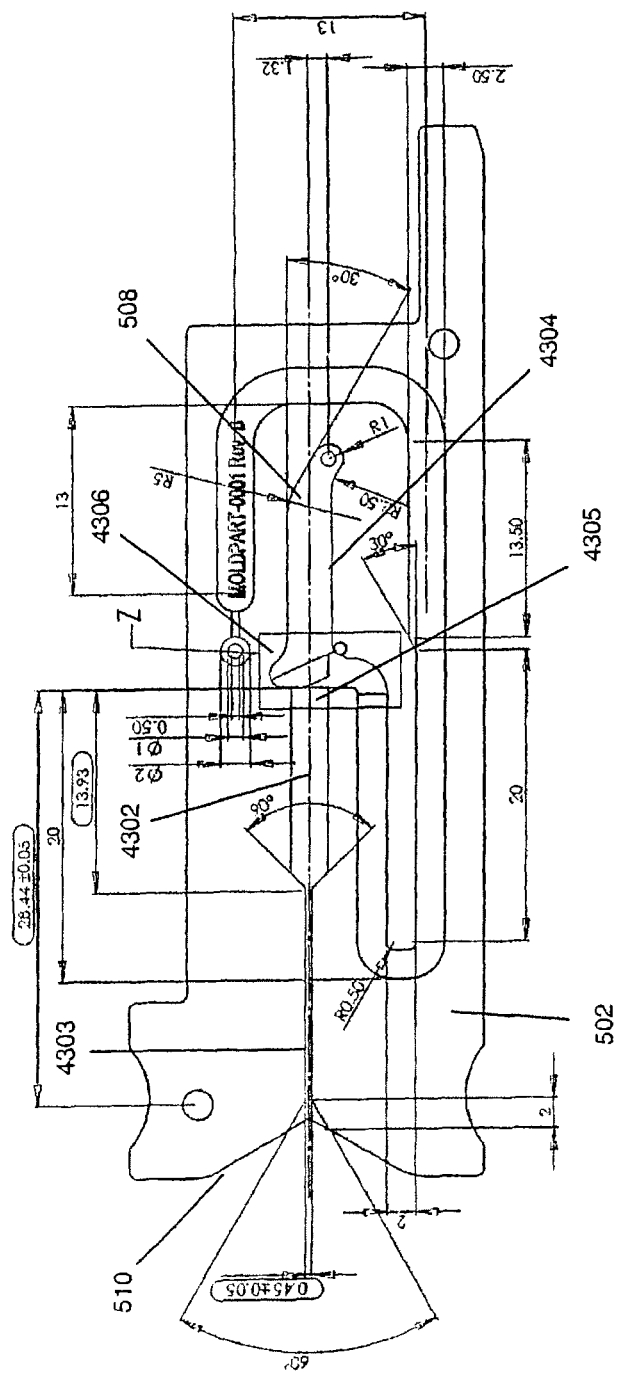
FIG. 7 shows a plan view of an exemplary embodiment of an assay device from above, including component dimensions (mm)

Referring to FIG. 7, an exemplary embodiment of the device has an inlet 510 at one end of the strip, the inlet 510 is connected to the channel network 508 such that sample liquid received at the inlet can enter the channel network. The channel network 508 has a first channel portion 4302 forming a reagent zone. In an exemplary embodiment the first channel portion 4302 is connected directly to the inlet 510. In other exemplary embodiments, an inlet channel 4303 connects the inlet 510 and first channel portion 4302.

The first channel portion 4302 is connected to a second channel portion 4304 at a junction 4305. In an exemplary embodiment the plane of the junction is substantially orthogonal to the main longitudinal axis of the second channel portion. The first and second channel portions can have a common longitudinal axis.

The first channel portion 4302 is generally rectangular in cross-section, although it may have a different cross-sectional shape, e.g. circular. At the junction 4305 the first channel portion 4302 has a cross-sectional area $A^1$ which is less than the cross-sectional area $A^2$ of the second channel portion 4304 at the junction 4305. The difference in cross-sectional area of the first and second channel portions at the junction 4305 provides a capillary stop 530, as described above. A liquid sample deposited at inlet 510 flows into first channel portion 4302 (e.g. by capillary action) and on reaching the capillary stop 530 the liquid sample meniscus forms a liquid sample:air interface with air contained in the second channel portion. The interface is positioned proximal the junction 4305. Cross-sectional area $A^1$ is at least about 0.375 mm$^2$ and $A^2$ is about 4.67 mm$^2$. The ratio of $A^1$:$A^2$ is about 1:12.

Figure 8:
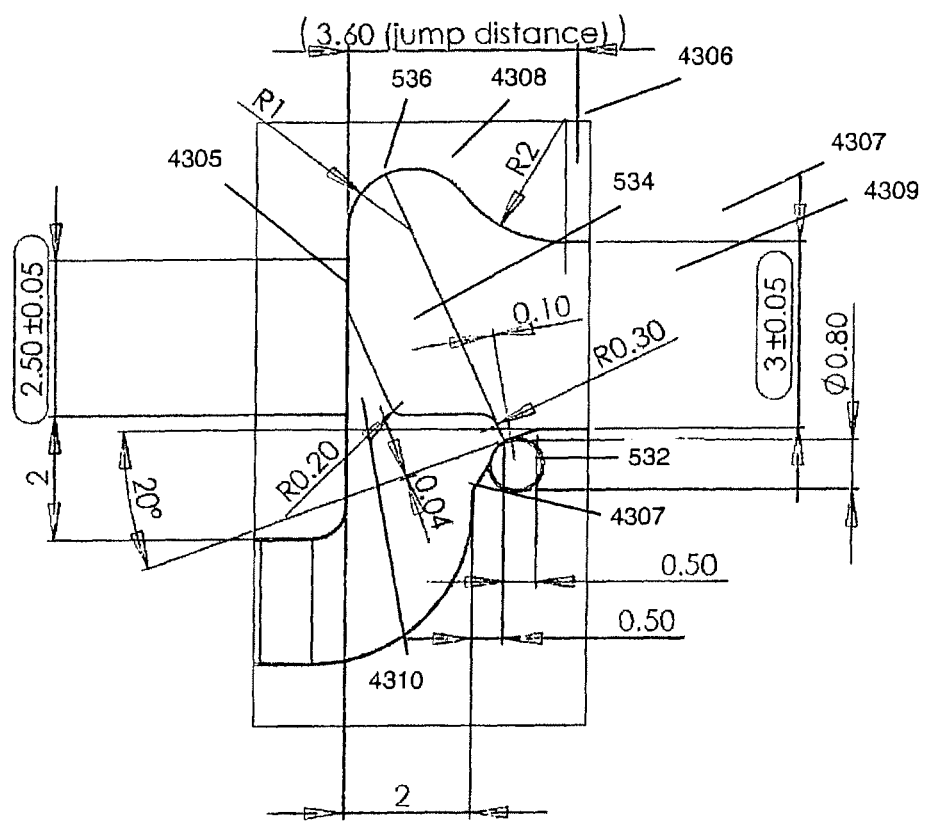
FIG. 8 shows an enlarged view of the interface zone Z from FIG. 7.
Figure 9:
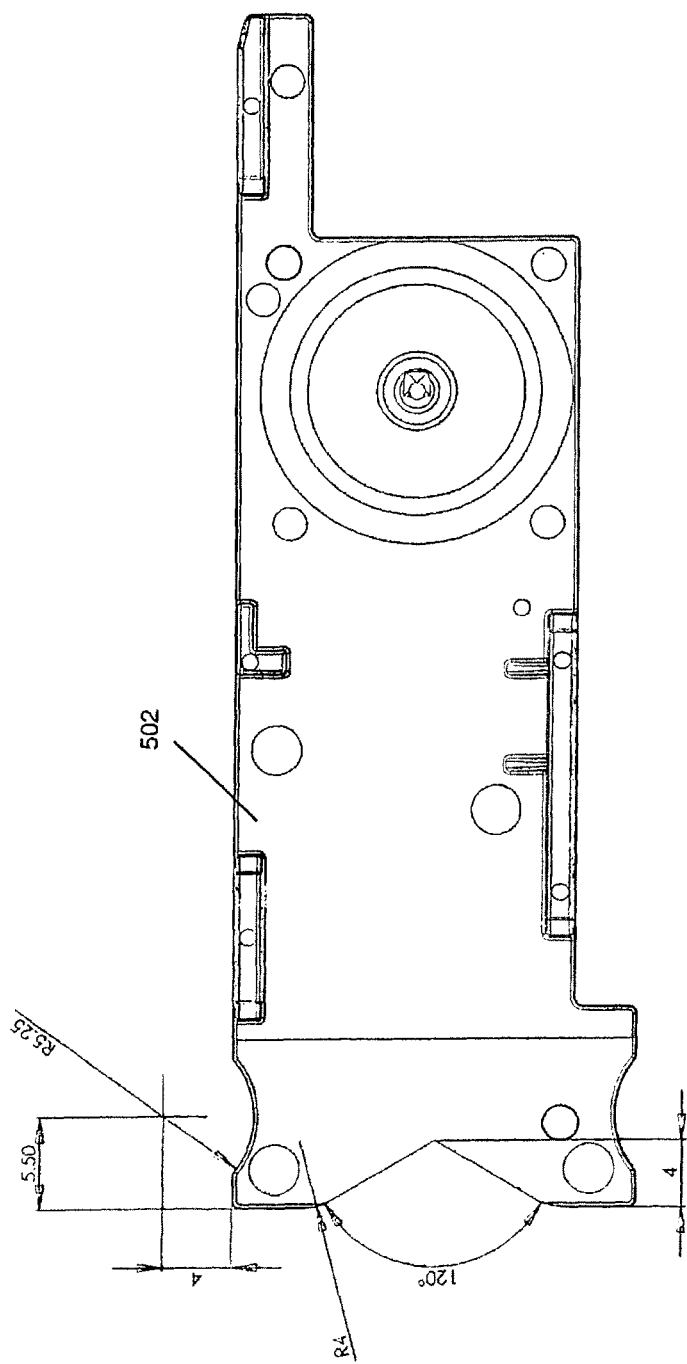
FIG. 9 shows a plan view of the upper part of an assay device (excluding buffer pouch)

Referring to FIGS. 7 and 8, adjacent the junction 4305, the second channel portion has a tapered neck region 4306 in which the width and height of the second channel portion 4304 increases when moving along the second channel portion from the liquid inlet 520 towards the junction 4305. The tapered neck region 4306 provides an increase in the width of the second channel portion from width w6 distal to junction 4305 to width w5 at the junction 4305 and an increase in the height of the second channel portion from height h3 distal to the junction 4305 to height h2 at the junction 4305.

Referring to FIG. 8, the tapered neck region 4306 of the second channel portion further comprises a bend portion in which the flow path defined by the second channel portion 4304 is changed from a direction that is substantially toward the junction 4305 to one that is substantially across the junction 4305. The bend portion is formed by an inside wall 4307 and an outside wall 4308 of the second channel portion 4304. The outside wall 4308 contains a corner 536 and the inside wall 4307 has a means 532 to retard the flow of liquid towards the junction 4305. The means 532 can be a capillary stop. The outside wall 4308 also comprises, at least partially, the junction 4305 of the first and second channel portions.

Between the corner 536 and the capillary stop 532 the base of the second channel portion has a slope or chamfer 534 which connects a region 4309 of the second channel portion 4304 that is distal to the junction 4305 and has height h3 with a region 4310 of the second channel portion 4304 that is proximal the junction 4305 and has height h2, wherein h2>h3. The slope 534 extends obliquely across the second channel portion from a region proximal the capillary stop 532 towards the opposing channel wall and corner 536. The upper edge of slope 534 extends from a region proximal the capillary stop 532 at the inside wall 4307 of the bend portion across the second channel portion 4304 slanting forwards towards the junction 4305. The upper edge of slope 534 extends from the region near the capillary stop 532 obliquely forwards towards the junction 4305 and towards a region of the second channel portion having a greater width. The lower edge of slope 534 contacting the region 4310 of second channel portion 4304 having height h2 makes an angle of about 20° (e.g. at least about 15°, at least about 30°, at least about 35°, less than about 45°, less than about 40°) with the plane of junction 4305. The oblique direction of the slope across the second channel portion towards the junction can thus also be described as an oblique slant of about 70° (e.g. at least about 75°, at least about 65°, at least about 60°, at least about 55°, less than about 45°, less than about 50°) from a main width w2 of the second channel portion 4304, wherein the main width w2 is perpendicular to the main longitudinal axis of the second channel portion 4304 extending towards the junction 4305.

The upper edge of slope 534 (distal to junction 4305) at its most distal from the junction, and in the region of capillary stop 532, is about 2.5 mm from the wall of the second channel portion 4304 in which the junction 4305 is formed in a direction along a line parallel to the main longitudinal axis of the second channel portion. This distance d2 is about 2.5 mm (e.g. at least about 2.0 mm, at least about 3.0 mm, less than about 5.5 mm, less than about 5.0 mm). The distance between lower edge of slope 534 (proximal to junction 4305) at its most distal from the wall of the second channel portion 4302 in which the junction 4305 is formed, and in a direction along a line parallel to the main longitudinal axis of the second channel portion 4304, is called d3 and is about 0.5 mm (e.g. at least about 0.4 mm, at least about 1.0 mm, less than about 2.0 mm, less than about 1.8 mm). The shortest distance from the upper edge of slope 534 to the lower edge of slope 534 is d4, which is about 2.0 mm (e.g. at least about 1.5 mm, at least about 2.5 mm, less than about 3.0 mm, less than about 3.5 mm, less than about 4.0 mm).

The slope 534 has an angle of inclination θ of about 8° (e.g. at least about 5°, less than about 15°, less than about 25°), being the angle of inclination of the slope 534 from the base of the second channel portion 4304 adjacent the junction 4305 and having height h3.

Slope 534 and capillary stop 532 control movement of liquid through the second channel portion 4304 from liquid inlet 520 towards junction 4305. Liquid moving through the second channel portion 4304 from liquid inlet 520 towards junction 4305 has an advancing liquid meniscus forming a liquid:gas interface that is advancing towards junction 4305. Prior to reaching junction 4305 the advancing meniscus encounters capillary stop 532 which retards the movement of the advancing liquid meniscus along the inside wall 4307 of the bend portion. Capillary stop 532 thus acts to steer the liquid:gas interface around the corner in which capillary stop 532 is located, as described above. The advancing liquid:gas interface thus moves down chamfer 534 and across the face of the junction 4305 of the first and second channel portions.

When a liquid sample is contained in the first channel portion 4302 forming a liquid sample:air interface at the junction, movement of liquid through the second channel portion towards the junction 4305 and across the face of the junction 4305 acts to displace the air from the liquid sample:air interface and form an interface of the liquid sample and liquid contained in the second channel portion, e.g. buffer liquid.

The bend portion, capillary stop 532 and slope 534 act together to advance the flow of liquid in the second channel portion 4304 towards the junction 4305 initially around the outside wall 4308 of the bend portion and past corner 536, thereby directing liquid flow across the wall in which the junction 4305 is formed. This acts to displace air from the liquid sample:air interface and form the liquid sample:liquid interface with minimum retention of air bubbles at the interface. Excess liquid flowing in the second channel moves into overflow channel 524 until it reaches vent 526.

A liquid sample:liquid interface is thereby formed at the junction 4305 by flowing liquid in the second channel portion 4304 across a face of the liquid sample:air interface so as to displace the air from that interface and progressively decrease the area of the liquid sample:air interface until the air is displaced and the liquid sample:air interface is replaced by a liquid sample:liquid interface.

During flow of liquid in the second channel portion 4304 across the liquid sample:air interface, liquid sample in the first channel portion is held substantially static. Once the liquid sample:liquid interface is formed and flow of liquid in the second channel part 4304 and overflow 524 has stopped the liquid sample:liquid interface is also substantially static with no bulk movement of liquid occurring across the interface, in either direction.

To avoid breach of the liquid:air interface, e.g. where liquid in the first channel portion breaches the capillary stop formed at the junction 4305 and enters the second channel portion 4304, the capillary stop formed at junction 4305 is designed to withstand normal capillary forces exerted by the sample fluid. However, the capillary stop can be breached if the force of the sample fluid flowing in the first channel portion is further increased, which may happen if excess sample is applied at the inlet or an external force is applied to the assay device.

It is also preferred that the liquid:liquid interface is stable and substantially static. In particular, the passive movement of particles across the interface, e.g. from the liquid sample into the buffer liquid, should be kept to a minimum, e.g. in order to avoid unwanted cross-reaction of buffer substrate with components of the liquid sample and to minimise loss of magnetically susceptible particles from the liquid sample into overflow 524.

Figure 14:
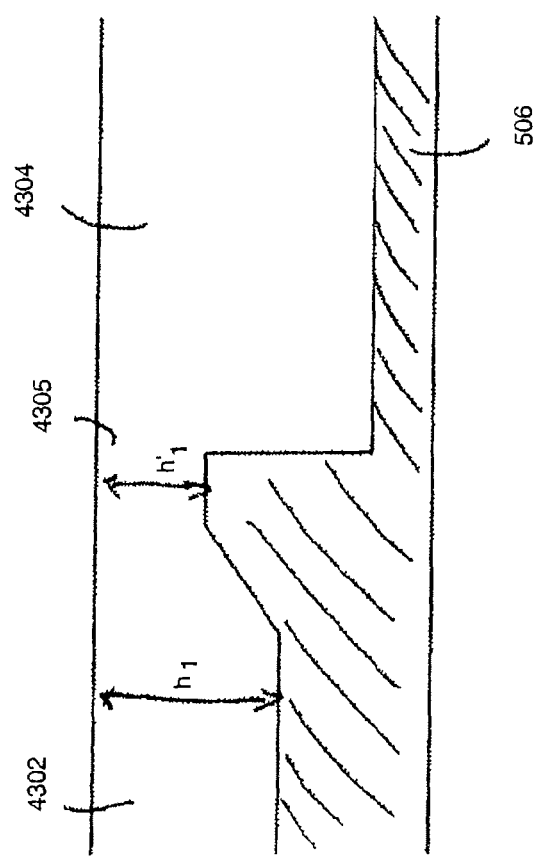
FIG. 14 shows an enlarged view of the junction in one exemplary embodiment of the assay device.
Figure 21:
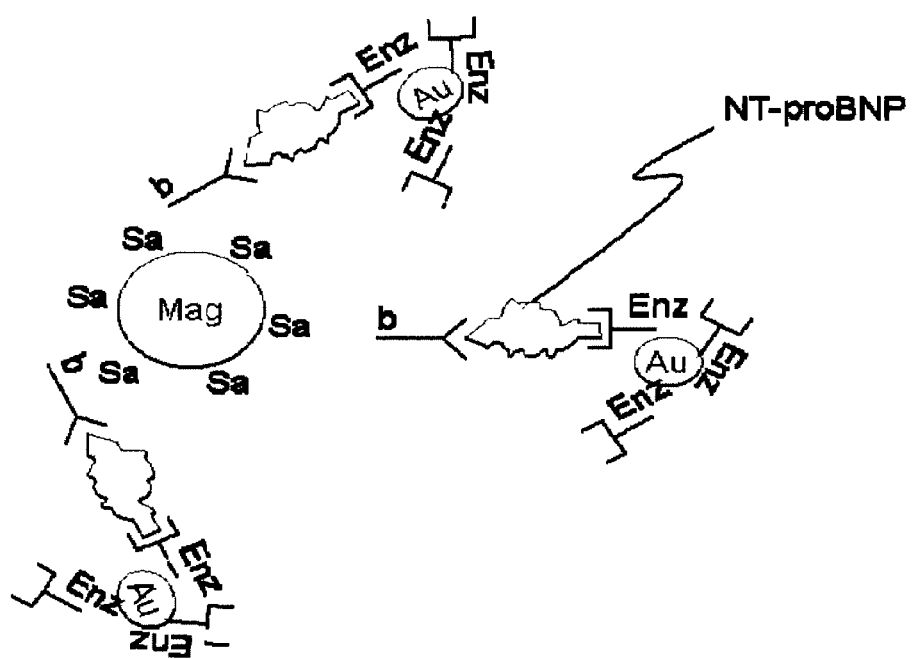
FIG. 21 shows a diagram of the detection of NT-proBNP.

Prevention or reduction of interface breach can be provided in one or a combination of ways. In a first such exemplary embodiment, and referring to FIG. 14, the height ($h'_1$) of the first channel portion 4302 at the junction 4305 is less than the height ($h_1$) of the main body of the first channel portion 4302 (i.e. $h_1 > h'_1$). The base of the first channel portion 4302 includes a ramp extending upwards towards the junction 4305 (as shown in FIG. 21), or alternatively (or additionally) extending downwards towards the junction 4305 from the lid of the first channel portion 4302. The ramp connects the parts of the first channel portion having heights $h_1$ and $h'_1$. The first channel portion 4302 thus has restricted dimensions at the junction 4305 compared to the main body of the channel.

The reduction in height of the first channel portion 4302 from $h_1$ to $h'_1$ has the effect of increasing the difference in height between the height of the first channel portion 4302 at junction 4305 (this being $h'_1$) and the height of the second channel portion 4304 at junction 4305 ($h_2$). This increases the capillary stop.

In combination with, or as an alternative to, the use of a change in height of the first channel portion 4302 proximal the junction 4305 one or more of the internal wall(s) (optionally including base and/or lid) of the first channel portion can be coated in a hydrophobic material at, and or proximal to, the junction 4305. This coating can be in the form of a hydrophobic patch, line or ring extending around the circumference of the first channel portion. The patch, line or ring can have a thickness of about 3 mm (e.g. at least about 0.5 mm, at least about 1 mm, at least about 2 mm, at least about 3 mm, at least about 5 mm).

The possibility of interface breach occurring can also be prevented or reduced by controlling the quantity of sample fluid deposited at the inlet 510. Sample fluid deposited at inlet 510 and in fluid connection with sample fluid in the first channel portion 4302 provides a head of pressure and the capillary stop pressure provided at junction 4305 is required to equal or exceed this in order to provide a stable liquid:air interface. In some embodiments deposit of an excess of sample fluid is prevented by partitioning the inlet into at least two compartments. One or more first compartments are in fluid connection with the first channel portion 4302 and, in combination with the first channel portion 4302, have a predetermined total volume ($V_t$) configured to provide a head of pressure that will not exceed the capillary stop pressure at junction 4305. In a preferred embodiment $V_t$ is about 5 μl or about 10 μl (e.g. at least about 2 μl, at least about 5 μl, at least about 10 μl, less than about 30 μl, less than about 20 μl, less than about 15 μl). Excess sample fluid deposited at the inlet overflows from the first compartment(s) into one or more second compartments not fluidly connected to the first channel portion 4302.

In an exemplary embodiment where the liquid sample is blood a filter is positioned at inlet 510 to prevent entry of red blood cells into first channel portion 4302 but allow entry of the fluid parts of the blood sample.

In an exemplary embodiment the use of a second liquid introduced to the second channel portion of assay device 500 to form the liquid sample:liquid interface is replaced by inclusion of a flowable media in the second channel portion. On introduction of the liquid sample to the first channel portion 4302 a liquid sample:flowable media interface is formed proximal the junction 4305. Magnetic transfer of magnetically susceptible particles across the interface into the flowable media and to the working electrode is then performed as described herein with respect to the other embodiments described. In such embodiments the assay device 500 does not require integration of reservoir 507.

The flowable media can be a liquid. However, in exemplary embodiments, the flowable media is a viscous liquid or gel. For example, the gel can be a matrix or electrophoresis gel such as an agarose or polyacrylamide gel, or other crosslinked polymer. The gel should provide a continuous flowable media path between the interface and sensor (e.g. working electrode 516w) allowing for movement of magnetically susceptible particle:first binding agent:analyte complexes from the interface through the gel to the sensor. The gel can also contain substrates (e.g. ABTS and $H_2O_2$) required to detect analyte at the sensor.

The first channel portion 4302 contains reagents. The reagents include multiple magnetically susceptible particles (e.g. at least about 50, at least about 100, at least about 150 magnetically susceptible particles) and a first binding agent configured to bind an analyte. The first binding agent is configured to also bind to the magnetically susceptible particles such that complexes of analyte:first binding agent:magnetically susceptible particle can be formed when the reagents are contacted with a liquid sample containing the analyte. These complexes can be magnetically moved through the liquid sample:liquid interface.

In one exemplary embodiment the reagents include a second binding agent configured to bind the analyte at a different spatial location (epitope) on the analyte to the first binding agent. The first and second binding agents can both be bound to an analyte molecule at the same time to form a "sandwich" complex. The sandwich complex can comprise first and second binding agents bound to the analyte and magnetically susceptible particle bound to the first binding agent. These complexes can be magnetically moved through the liquid sample:liquid interface.

The first or second binding agent can be conjugated to a detectable marker. The detectable marker can be any detectable label, e.g. enzyme label, fluorescent marker, radiolabel. An enzyme label can provide or cause a detectable signal, e.g. an electrochemical signal—oxidation or reduction at an electrode—following interaction with a substrate of the enzyme. A fluorescent marker can provide an optical signal—fluorescence—which can be detected by an optical sensor or scintillation counter. A radiolabel can provide an electromagnetic signal which can be detected by a sensor that can detect the electromagnetic radiation.

In an exemplary embodiment, the second binding agent is conjugated to an enzyme label, e.g. horse radish peroxidise. Second binding agent:enzyme label conjugates are further absorbed onto a colloidal sol particle, e.g. colloidal gold sol particles. The colloidal sol particles can have a diameter of about 20 nm or about 40 nm.

The magnetically susceptible particles and first binding agent are modified to incorporate complementary linkers, e.g. one of biotin and streptavidin, in order to provide conjugates of the magnetically susceptible particles and first binding agent. The magnetically susceptible particles and first binding agent can be deposited in the first channel portion in pre-conjugated form, or can be deposited separately such that the conjugates form on mixing of the reagents in the liquid sample.

In an alternative exemplary embodiment a mixture of liquid/fluid reagents is introduced to the first channel portion 4302 and is then dried to provide a dry mixture reagent deposit.

In an exemplary embodiment, the analyte for detection in a blood sample contained in the first channel portion is NT-proBNP (e.g. human NT-proBNP). The first and second binding agents are anti-NT-proBNP antibodies that bind different epitopes on NT-proBNP. The first binding agent is:
a monoclonal mouse anti-human NT-proBNP antibody 15C4 (HyTest Ltd., Intelligate 6th floor, Joukahaisenkatu 6, 20520, Turku Finland; Catalogue #:4NT1) and the second binding agent is chosen from:
monoclonal mouse anti-human NT-proBNP antibody 15F11 (HyTest Ltd., Intelligate 6th floor, Joukahaisenkatu 6, 20520, Turku Finland; Catalogue #:4NT1);
monoclonal mouse anti-human NT-proBNP antibody 29D12 (HyTest Ltd., Intelligate 6th floor, Joukahaisenkatu 6, 20520, Turku Finland; Catalogue #:4NT1).
The first binding agent can be biotinylated to facilitate conjugation to streptavidin coated magnetically susceptible particles. The second binding agents can be conjugated to horse radish peroxidise and 20 nm or 40 nm diameter colloidal gold sol particles.

Other antibodies to NT-proBNP are publicly available, e.g. those available from HyTest Ltd., Intelligate 6th floor, Joukahaisenkatu 6, 20520, Turku Finland, e.g. monoclonal mouse anti-human NT-proBNP antibodies 5B6, 7B5, 13G12, 11D1, 16E6, 15D7, 24E11, 28F8, 18H5, 16F3 (Catalogue #:4NT1).

In an exemplary embodiment in the electrode set 516w, 516c, 516r positioned in the second channel portion 4304 the working electrode 516w is positioned closest the junction 4305 at a distance of about 3.6 mm to the centre line of the electrode from the junction (e.g. at least about 2 mm, at least about 3 mm, at least about 3.5 mm, at least about 4 mm, at least about 5 mm, at least about 6 mm, less than about 8 mm, less than about 10 mm). Electrode 516w has a width of about 2.4 mm (e.g. at least about 2.0 mm, at least about 2.5 mm, less than about 3.5 mm, less than about 3.0 mm). The width of electrode 516w is sufficient to tolerate small variations in the positioning of magnetically susceptible particles and retain the ability to detect an electrochemical signal produced by reagent-substrate interaction at those particles. Between the working electrode and reference electrode 516r is a counter electrode 516c. The working and counter electrodes are made from carbon paste and the reference electrode from silver paste. The reference electrode is an Ag/AgCl reference electrode and is about 1 mm wide (e.g. at least about 0.6 mm, at least about 0.8 mm, less than about 2.0 mm, less than about 1.4 mm, less than about 1.2 mm) and about 5 mm from the centre line of the electrode from the junction 4305 (e.g. at least about 4 mm, at least about 6 mm, less than about 9 mm, less than about 12 mm).

In one exemplary embodiment the enzyme label is horse radish peroxidase and the liquid in the second channel portion 4304 is a reaction buffer containing sodium acetate buffer, hydrogen peroxide substrate, and the redox mediator 2,2'-azino-bis-(3-ethylbenzo-thiazoline-sulfonic acid) (ABTS), as described above. In one exemplary embodiment the buffer liquid is 10 mM ABTS, 10 mM $H_2O_2$, 150 mM KCl, 125 mM sodium acetate; 0.1% v/v Tween-20™, made to a final pH 4.2.

In other embodiments where detection of analyte in the second channel portion is other than by electrochemical detection—e.g. detection of fluorescence or colour—the sensor may comprise a region of the second channel portion at which a signal, e.g. fluorescence or colour, can be detected. In such embodiments the sensor can comprise a transparent portion of the device permitting interaction with a detector, e.g. a photodetector or scintillation counter, in meter 400.

Figure 16A:
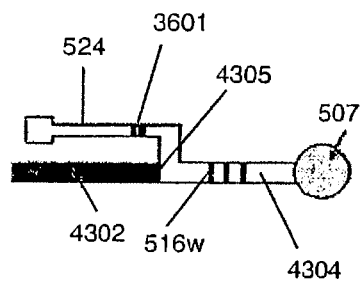
FIGS. 16A-D show on-board control configurations.

The device can have one or more "on-board controls" to serve as checkpoints for the proper operation of the device. For example, a first on-board control can be the use of one of the electrodes 516w, 516c, 516r to detect flow of liquid from the liquid inlet 520 towards the junction 4305. Flow of liquid through the second channel portion 4304 will form a conductive bridge between two of the electrodes 516w, 516c, 516r. By operating meter 400 during liquid flow through the second channel portion 4304 towards the junction 4305 to detect current flow through two electrodes, e.g. the working and counter electrodes 516w and 516r, the meter can detect progress of the liquid towards the junction 4305. Referring to FIG. 16A, a second on-board control can be the use of an electrode or electrode pair 3601 positioned in overflow channel 524 to detect flow of liquid into the overflow channel and provide an indication of liquid sample:liquid interface formation at junction 4305.

Figure 16B:
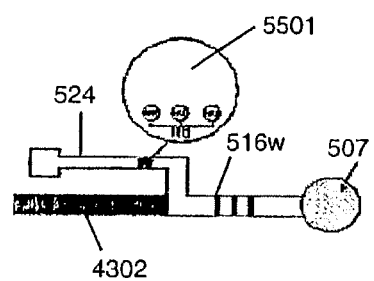
Figure 16C:
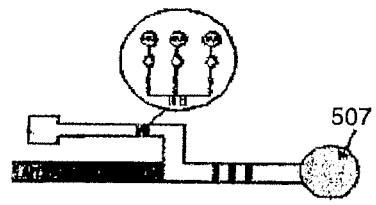
Figure 16D:
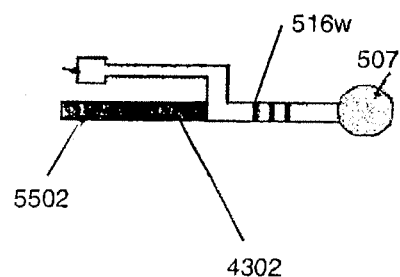

Further on-board controls can act as controls for the assay being performed. For example, because substrates or reagents can decompose or lose activity over time, one may wish to test for activity of these substrates or reagents, e.g. of a substrate contained in liquid introduced into the second channel portion 4304. In one exemplary arrangement the enzyme label can be horse radish peroxidase, which catalyses conversion of hydrogen peroxide and ABTS to water and oxidised-ABTS. Hydrogen peroxide and ABTS are provided in the buffer liquid introduced to the second channel portion 4304. Referring to FIG. 16B, the presence and/or activity of the hydrogen peroxide and ABTS can be verified by immobilizing a predetermined quantity of the horse radish peroxidase enzyme label 5501 at electrode(s) 3601 in the overflow channel 524. Active buffer liquid components reaching the overflow will be catalysed and produce oxidized ABTS and an electrochemical signal that can be detected by electrode(s) 3601. Detection of a signal is indicative of active buffer components and serves to verify the validity of the determination made at working electrode 516w. Referring to FIG. 16C, in an alternative arrangement the immobilized horse radish peroxidase can be substituted for an immobilized complex of magnetically susceptible particle:first binding agent:analyte:second binding agent, wherein the horse radish peroxidase is conjugated to the second binding agent. Such an arrangement may more accurately reflect the form of ternary complex formed at the working electrode 516w and provide an improved control.

Figure 15A:
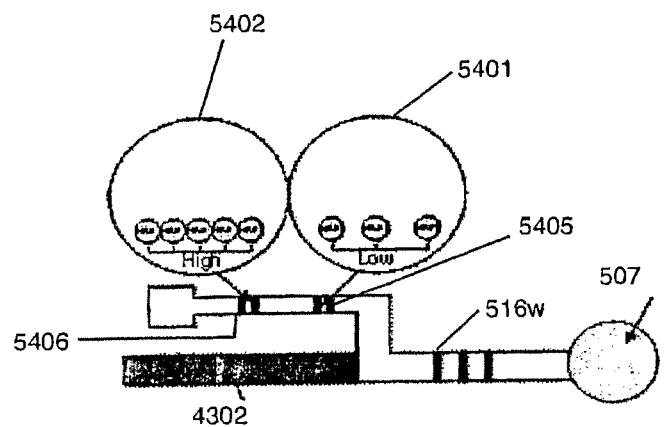
FIGS. 15A-B show on-board control configurations.
Figure 15B:
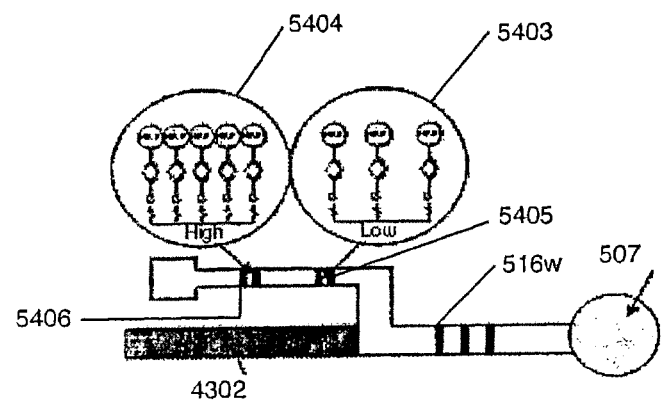

Variations of the controls illustrated in FIGS. 16B and 16C are illustrated in FIGS. 15A and 15B respectively. Referring to FIG. 15A, first and second electrodes (or pairs of electrodes) 5405, 5406 are provided in the overflow channel 524. A predetermined amount of horse radish peroxidase is immobilized 5401 at the first electrode pair 5405 and will produce a first electrochemical signal $R_1$ when buffer liquid containing hydrogen peroxide and ABTS is present. A second predetermined amount of horse radish peroxidase is immobilized 5402 at electrode pair 5406, wherein the second amount is larger than the first amount at electrode 5401. The second amount of horse radish peroxidase will produce an electrochemical signal $R_2$ when buffer liquid containing hydrogen peroxide and ABTS is present, where $R_2 > R_1$. $R_2$ and $R_1$ can be configured to provide high and low control electrochemical signals, with respect to the selected assay and provide verification of the operable range of the assay. Referring to FIG. 15B, in an alternative arrangement the immobilized horse radish peroxidase can be substituted for an immobilized complex of magnetically susceptible particle:first binding agent:analyte:second binding agent, wherein the horse radish peroxidase is conjugated to the second binding agent. Such an arrangement may more accurately reflect the form of ternary complex formed at the working electrode 516w and provide an improved control.

In a microfluidic assay involving the interaction of a substrate with reagents in a fluid or liquid, on-board controls can be used to assess the state of the substrate(s) and/or reagent(s). For example, they can validate the activity of the substrate(s) and/or reagent(s) such that a valid assay result can be obtained. In another example, they can indicate that one or more of the substrate(s) and/or reagent(s) have lost or gained an activity or chemical state (e.g. oxidized/reduced), indicating that the assay result will not be valid within normal parameters and may need to be deemed void or be corrected. On-board controls of this kind can be performed independently of the presence of the sample, and provide information on the reagents and substrates used in the assay device.

In exemplary embodiments of the assay device, in which reagent(s) interact with sample in a first zone and are then moved into a different media, e.g. different liquid or fluid, in which the reagent(s) interact with substrate(s) resulting in a signal that is detected at different zone, an on-board control that indicates the activity or viability of the reagent(s) and/or substrate(s) is provided. In exemplary embodiments electrochemical detection of substrate and/or reagent activities is used to provide control values. In exemplary embodiments where dry reagent or substrate is used in the assay the on-board control will use a corresponding dry reagent or substrate, which may be re-hydrated prior to detecting the control signal.

The on-board control for activity of the reagents comprises a predetermined quantity of reagent, e.g. enzyme reagent, deposited at or adjacent a defined location in the microfluidic network 508. In an exemplary embodiment this quantity of reagent is deposited at the same time as reagent is deposited in the reagent zone for interaction with the sample and is from the same batch of reagent. The reagent is deposited in the second channel portion 4304 at a location downstream of the junction 4305 with respect to the direction of flow of the second liquid, i.e. in the overflow 524. This reagent control is positioned in the overflow channel 524 such that reaction of the reagent and substrate does not affect or interfere with signal detection at the working electrode 516w which relies on the interaction of reagent bound to magnetically susceptible particles from the sample with substrate in the second liquid.

A predetermined quantity of reagent is deposited in the overflow 524 at or adjacent a reagent control zone. In an exemplary embodiment the reagent control zone has one or more detection electrodes 3601, e.g. a set of three electrodes (working, counter and reference), to detect the reagent control signal. Following formation of the liquid sample:second liquid interface and flow of the second liquid into the overflow 524, substrate contained in the second liquid reacts with reagent at the reagent control zone to produce a signal that is detected by meter 400.

The signal may be electrochemical or optical, for example. In an exemplary embodiment the reagent is horse radish peroxidase (HRP) and substrates are ABTS and $H_2O_2$. The reaction of HRP with ABTS and $H_2O_2$ yields oxidized ABTS which can be electrochemically detected by the electrode set. Accordingly, the extent of oxidation of ABTS (and effectively loss of active (reduced) ABTS for conversion to oxidized ABTS by reaction with reagent) can be detected in the second liquid at the working electrode prior to interaction with reagent to provide a substrate control.

In an exemplary embodiment a substrate control is also provided. The activity of the substrate may be determined at any chosen location in the second channel portion 4304 (or in a further channel portion provided for this purpose) provided that location is substantially free of reagent. In an exemplary embodiment the activity of the substrate is determined in the second liquid upstream of the junction 4305 and prior to transfer of magnetically susceptible particles across the junction 4305 into the second liquid. Accordingly, the substrate control signal indicates activity of the substrate in the absence of reagent. In an exemplary embodiment the substrate control signal is determined at electrodes 516w, 516r, 516c.

Determining a control signal for substrate activity in the absence of reagent provides a signal for the substrate at zero reagent concentration (i.e. [R]=0). Determining a control signal for reagent activity in a reagent control zone provides a signal at known reagent concentration (e.g. [R]=1). The control signal values can be plotted against reagent concentration to provide a curve or line. Where more than one reagent control is provided the data from the additional reagent control(s), having different reagent concentrations, can also be used to plot the curve or line. This can be compared against a standard curve or line to determine the extent of deterioration of substrate or reagent activity and to calculate any adjustment that is required to be made to the assay result. In an exemplary embodiment the control signal detected is an electrochemical signal (e.g. μA).

Accordingly, in one exemplary embodiment, following formation of the liquid:air interface second liquid is forced from buffer pouch 507 into second channel portion 4304 such that the second liquid is directed towards junction 4305. Prior to contact with the liquid:air interface, the second liquid contacts electrodes 516w, 516r and 516c and a substrate control signal is detected. Second liquid continues to flow towards junction 4305 to form the liquid sample:second liquid interface and second liquid flows into overflow 524 to contact the reagent control zone where the reagent control signal is detected. The substrate control and/or reagent control signals are processed by meter 400 to determine the activity of the substrate and/or reagent. The processing step can involve comparing the substrate control and/or reagent control signals against standard reference values for reagent and/or substrate activity, e.g. against an activity value for a laboratory standard. The determined control activity may be within a normal (expected) activity indicating that the assay may proceed and the assay result is valid. Alternatively the determined control activities may be outside tolerated ranges (e.g. activity too low) and the assay result may be indicated as 'Void'. In another exemplary alternative, by using the reagent control and substrate control values to determine the degree to which the activity of the substrate and/or reagent is diminished (or increased) a modification or correction may be applied to the assay result to provide a valid assay result that is displayed to the user. For example, the modification or correction assumes that the activity of all reagent and/or substrate contained in the assay device has deteriorated by the same amount or factor such that the assay result needs to be increased by a corresponding amount or factor.

In exemplary embodiments reagent activity is determined by detection of substrate activity, e.g. by detecting conversion of ABTS from reduced to oxidized form by the reagent. Thus, an on-board control for activity of substrate and reagent is provided by detecting the substrate activity (e.g. extent of oxidation of reduced ABTS substrate) at two positions in the second channel portion, each having different reagent concentrations. In one exemplary embodiment, one of the reagent concentrations can be zero. To ensure substrate activity is measured at zero reagent concentration it can be detected at the working electrodes prior to movement of magnetic particles across the junction.

Although the assay device provides for a stable, substantially static liquid sample:second liquid interface small quantities of liquid sample can be washed into the second liquid and into overflow 524. Reagent:magnetically susceptible particle complexes washed from the liquid sample into the second liquid will increase the quantity of reagent at the reagent control zone such that the reagent control signal detected is no longer a result only of interaction of the predetermined quantity of reagent deposited at the reagent control with the substrate but is affected by the presence of small quantities of additional reagent.

Figure 12A:
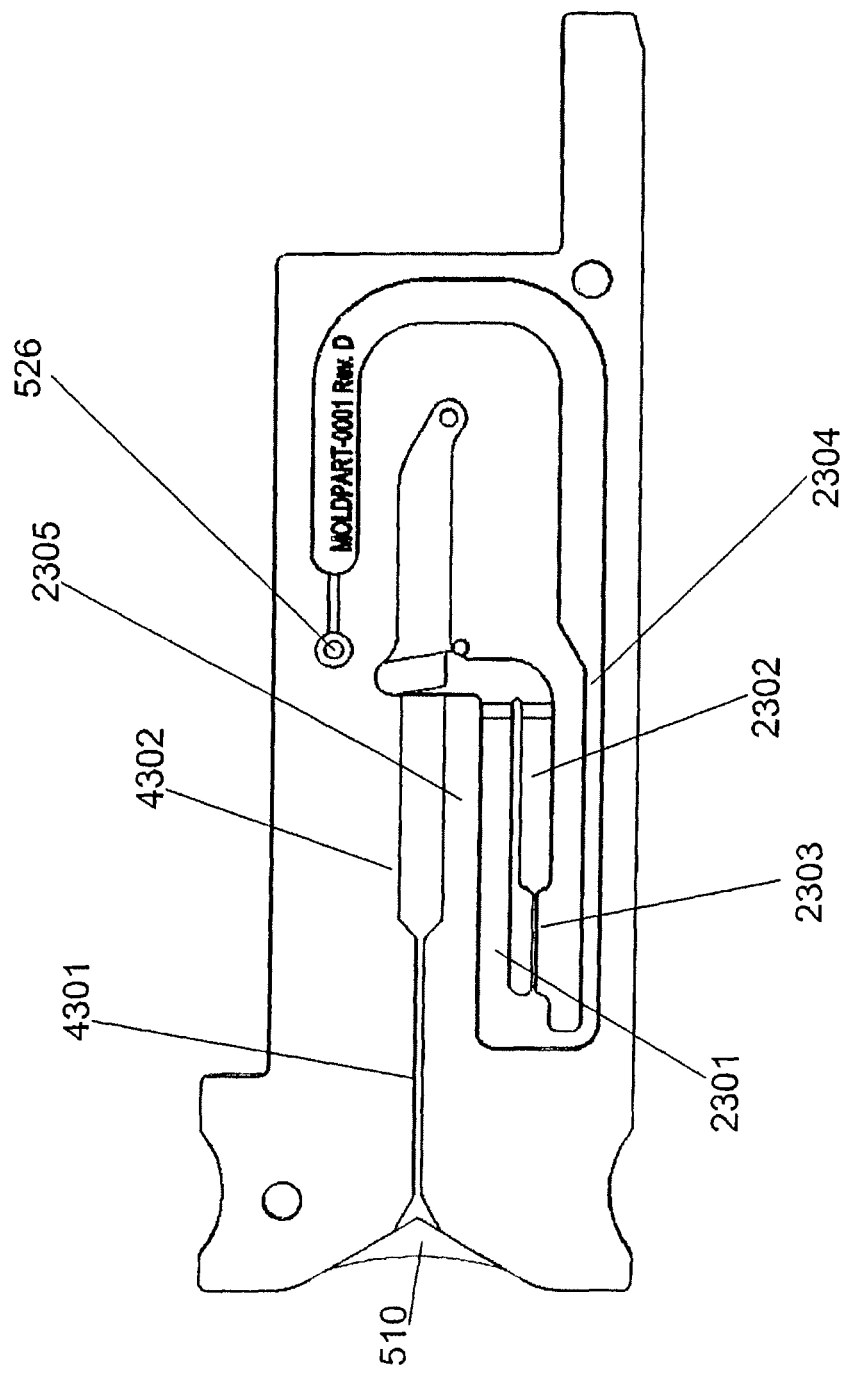
FIGS. 12A and 12B show plan views of the microfluidic network of one exemplary embodiment of the assay device (dimensions in FIG. 12B in mm)
Figure 12B:
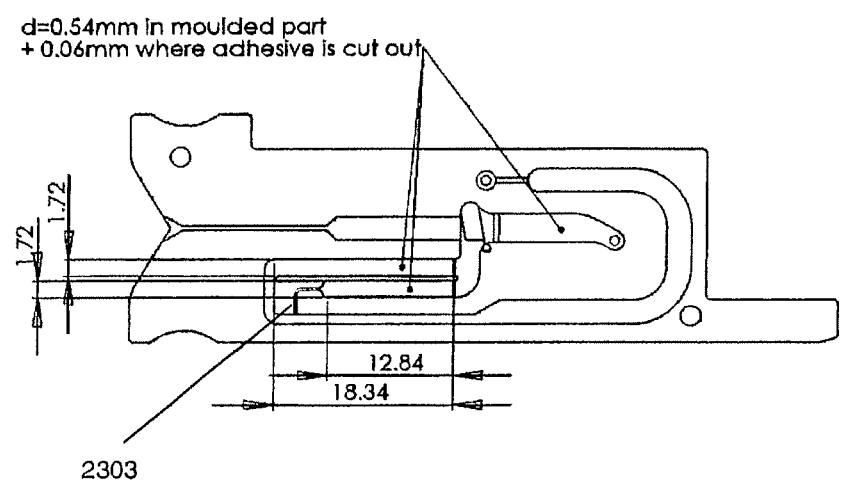

This problem can be overcome by partitioning the overflow channel into two parts. Referring to FIGS. 12A and 12B, the overflow channel is generally parallel to the first channel portion 4302 and is divided by a partition that is also substantially parallel to the first channel portion 4302 thereby forming a first overflow channel 2301 and a second overflow channel 2302. The first overflow channel 2301 provides an excess channel volume to receive second liquid, displacing air through vent 526 as the second liquid progresses along the first overflow channel 2301. This excess channel volume reduces the possibility of back-flow of the second liquid.

The second overflow channel 2302 is configured to receive at least some of the second liquid overflowing from the interface zone through an inlet. Distal to, and downstream of, the inlet the second overflow channel 2302 is tapered to form a narrow channel providing a vent 2303 through which air is dispelled as liquid fills the second overflow channel 2302. Vent 2303 is connected to the first overflow channel 2301. Vent 2303 is sufficiently narrow and hydrophobic that second liquid is substantially completely prevented from flowing through vent 2303 into the first overflow channel 2301. Accordingly, once filled the second overflow channel 2302 provides a defined volume of second liquid.

Particles washed away from the liquid sample:second liquid interface into the second liquid are carried in the second liquid close to the wall 2305 separating the first channel portion 4302 and first overflow channel 2301 and into the first overflow channel 2301. Second liquid free or substantially completely free of reagent is thereby carried into the second overflow channel 2302.

The reagent control zone is positioned in the second channel portion in which detection of the reagent control signal takes place in a defined volume of second liquid. Any reagent particles washed into the overflow from the liquid sample:second liquid interface flow into the first overflow channel 2301 and do not interfere with detection of reagent activity in the reagent control zone. Where the second liquid contains a predetermined known quantity of substrate, the defined volume of second liquid in the second overflow channel 2302 can be used to determine the extent of reaction of substrate and reagent and the activity of substrate and/or reagent.

In one exemplary embodiment, a single overflow channel is provided. In this arrangement the reagent control zone is positioned sufficiently far away from the interface zone that any particles washed into the second liquid overflow settle out in the overflow channel prior to reaching the reagent control zone such that detection of the reagent control signal takes place in second liquid that is free or substantially completely free of reagent.

Referring to FIG. 7, the overflow channel 524 has a length in the region of at least about 2 times the length of the second channel portion 4304 (e.g. at least about 2.5 times, at least about 3 times, at least about 4 times). The overflow channel defines a flow path initially substantially parallel to the flow path defined by the first channel portion, but thereafter may take any desired flow path to provide the required length of channel. In an exemplary embodiment the overflow channel may include one or more bend portions changing the direction of the flow path defined by the channel.

In an exemplary embodiment the reagent control zone is located in the overflow channel 524 at least about 20 mm (e.g. at least about 30 mm, at least about 40 mm, at least about 50 mm, at least about 60 mm, at least about 70 mm, at least about 80 mm, at least about 90 mm, at least about 100 mm) downstream of junction 4305. In an exemplary embodiment the reagent control zone is located downstream of a first bend portion in the overflow channel (not including any bend portion at the connection between the second channel portion and the overflow 524 immediately downstream of the junction 4305).

Interaction of Assay Device and Meter

Figure 2:
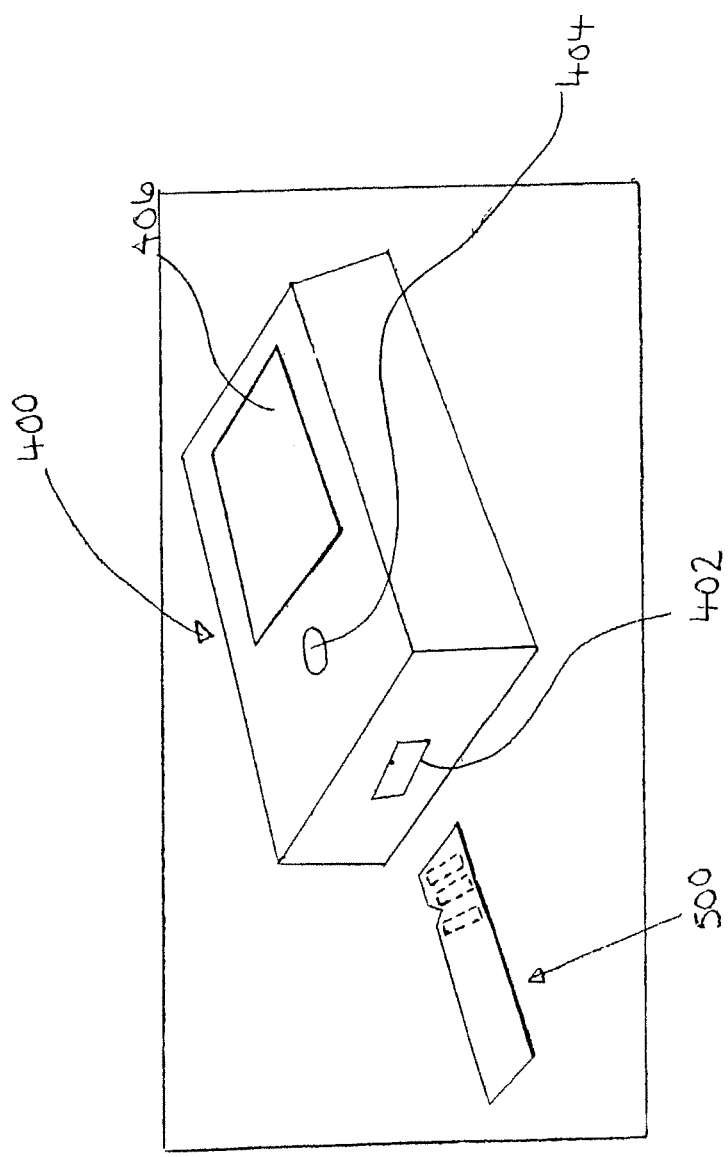
FIG. 2 is perspective view of an assay device and meter suitable for performing the assay method.

Referring to FIG. 2, meter 400 accepts test assay device 500 and includes display 406. The display 406 may be used to display images in various formats. Display 406 can also be used to display information to patients. Display 406 can provide a user with an input region 404. Input region 404 can include keys. User instructions and queries are presented to the user on display 406. The user can respond to the queries via the input region.

Meter 400 also includes an assay device reader, which accepts diagnostic test assay devices 500 for reading. The assay device reader can measure the level of an analyte based on, for example, the magnitude of an optical change, an electrical change, or other detectable change that occurs on a test assay device 500. For reading assay devices that produce an electrical change in response to analyte, the assay device reader can include electrical systems for measuring the detectable change, including, for example, a voltameter or amperometer.

Referring to FIG. 2 meter 400 is shown along with assay device 500. Meter 400 has a port 402 that receives assay device 500. A user of meter 400 inserts an assay device 500 through port 402 prior to performing an analysis of a sample.

Meter 400 is configured to operate assay device 500 when assay device 500 has been inserted through port 402. Meter 400 includes a liquid reservoir actuator, a magnetic actuator, electrochemical detector, and a processor. Reservoir actuator is configured to actuate reservoir 507 of device 500. The magnetic actuator is configured to manipulate (e.g., move and/or position) magnetically susceptible particles within microfluidic network 508 of assay device 500. The electrochemical detector is configured to determine the presence of analyte transported to electrodes 516$w$, 516$r$, 516$c$ by the magnetically susceptible particles. The electrochemical detector includes electrical contacts which respectively communicate with electrical contacts 518w, 518r, 518c of device 500 when received within meter 400.

In use, assay device 500 is inserted into meter 400 via port 402. A sample, e.g. a blood sample, is applied to inlet 510 of assay device 500. An amount of the sample (e.g., at least about 5 µl or 10 µl) moves into microfluidic network 508 (e.g. by capillary action). The sample interacts with reagents in the reagent zone. Target analyte is then transported to the detection zone where an electrochemical signal is recorded. Target analyte interacts with electrodes 516w, 516r, 516c and a signal is detected by the electrochemical detector. The processor interprets the signal detected by the electrochemical detector and displays information to a user on interface 406.
Description of Further Exemplary Embodiment—Detection of NT-proBNP In an exemplary embodiment, the analyte is N terminal pro-brain natriuretic peptide (NT-proBNP) and the sample material is whole blood from a human. The presence of NT-proBNP is indicative of a cardiac condition (i.e., a physiological condition related to the heart (e.g., a cardiac dysfunction such as heart failure)). Based at least in part on the result of the NT-proBNP determination, the presence of the cardiac condition can be determined. For example, it can be determined whether the human has experienced, is experiencing, or has a tendency to develop heart failure.

Several reagents are present within the reagent zone of the assay device. The reagents include the following species; a first antibody capable of binding to NT-proBNP, a second antibody capable of binding to NT-proBNP concurrently with the first antibody, an anti-coagulant to prevent clotting of the blood sample within the reagent zone, at least one magnetic particle, an enzyme label that can be used to produce a detectable species, buffer salts, and at least one colloidal particle. The first antibody can be modified with biotin, the second antibody can be conjugated with the enzyme label. The second antibody-enzyme conjugate can be adsorbed onto a colloidal gold sol particle to increase the number of antibody-enzyme conjugates. The magnetic particle can be coated with streptavidin, which can be used to capture the biotin modified first antibody. When the reagents interact with NT-proBNP a conjugate complex is formed, which can be represented stylistically in FIG. 21. The streptavidin coated magnetic particle can accommodate a number of biotin modified antibodies. The biotin modified first antibody binds to a first unique region of NT-proBNP. The second antibody-enzyme conjugate binds to a second unique region of NT-proBNP. Second antibody-enzyme conjugate is provided pre-associated with gold sol particles thus increasing the number of enzyme labels that become part of the NT-proBNP antibody complex. In an exemplary embodiment a first monoclonal antibody, clone 15F11 was biotin modified, and a second antibody, clone 24E11 was conjugated with HRP.

EXAMPLES

The following are non-limiting examples of certain embodiments.

Example 1

Detection of NT-proBNP in a Human Blood Sample

A human blood sample is added to the assay device 500 at inlet 510. The blood contains an amount of an analyte: N-terminal truncated pro-brain natriuretic peptide (NT-proBNP).

The sample of blood enters the first channel portion 4302, e.g. via capillary action, where it mixes with reagents in the reagent zone. The reagents in the reagent zone include streptavidin coated magnetically susceptible particles and biotinylated first binding agent which is an anti-NT-proBNP antibody 15C4 (HyTest Ltd.; Catalogue #:4NT) and horseradish peroxidase ("HRP") conjugated to a second binding agent which is anti-NT-proBNP antibody 15F11 or 29D12 (HyTest Ltd.; Catalogue #:4NT) (the antibody-linked enzyme). The assay device and included reagents are provided in a dry state. Addition of a liquid sample to the assay device (i.e., to the inlet and first channel portion) re-suspends dry reagents.

The reagents are re-suspended in solution with the blood, and form a mixture. The streptavidin coated magnetically susceptible particles bind to the biotinylated first binding agent to form a conjugate (the antibody-linked magnetically susceptible particle). The NT-proBNP in the blood is also bound by the first binding agent and a ternary complex of NT-proBNP bound antibody-linked magnetically susceptible particle is formed. A magnetic field is applied such that the magnetically susceptible particles undergo an induced motion (e.g., a periodic or oscillatory motion) to promote resuspension and mixing of the reagents with the sample.

The blood sample fills the first channel portion 4302 and on reaching junction 4305, the liquid forms a meniscus. The change in cross-sectional area of the channel at junction 4305 does not allow the blood sample to fill the second channel portion 4304. Rather, capillary pressure in the second channel portion exceeds any capillary forces that draw the sample liquid beyond junction 4305 into the second channel portion 4304. Junction 4305 thus acts as a capillary stop, preventing substantial liquid sample flow beyond that point. At this stage, a blood sample:air interface is formed by the blood meniscus at junction 4305.

After mixing of the reagents and blood sample, a magnetic field is applied to the first channel portion 4302. The applied field is manipulated so as to move the magnetically susceptible particles, and all components bound to them. The magnetically susceptible particles are magnetically moved along the first channel portion 4302 toward junction 4305.

A buffer liquid is added to the device at the second inlet 520. A buffer pouch 507 incorporated into the device delivers the reaction buffer. The buffer liquid contains 10 mM of the redox mediator 2,2'-azino-bis-(3-ethylbenzo-thiazoline-sulfonic acid) (ABTS), 10 mM $H_2O_2$, 150 mM KCl, 125 mM sodium acetate; 0.1% v/v Tween20, made to a final pH 4.2. The buffer does not contain analyte (NT-proBNP). The buffer liquid flows along the second channel portion 4304 to junction 4305, where the buffer liquid contacts the blood sample at the blood:air interface to form a blood:buffer interface.

The magnetically susceptible particles (and all that is bound to them) are moved across the blood:buffer interface by moving the applied magnetic field across the junction 4305 into the second channel portion 4304 and towards the working electrode 516w. The formation of the blood:buffer interface facilitates the magnetic movement of the magnetically susceptible particles (and all that is bound to them) from the blood to the buffer, leaving interfering sample components and analytes that are not of interest in the blood in the first channel portion 4302. The magnetically susceptible particles and all that is bound to them, including the NT-proBNP (in the form of a ternary complex of NT-proBNP with antibody-linked magnetically susceptible particle and antibody-linked enzyme) are transferred to the second liquid in the second channel portion 4304.

The magnetically susceptible particles bound to NT-proBNP are next moved to the working electrode 516w by manipulation of the applied magnetic field. The magnetically susceptible particles are magnetically positioned and held at the detection zone for an incubation time of e.g. 1 minute. Magnetically susceptible particles bound to NT-proBNP and the second binding agent:HRP conjugates are detected electrochemically by HRP mediated catalysis of hydrogen peroxide and ABTS to water and oxidised-ABTS. At the end of the incubation time the electrochemical current produced by the reduction of oxidized ABTS at the electrodes is measured at the working electrode for a measurement period (e.g. 3 seconds).

The detected electrochemical current is received in meter 400 and compared against a corresponding calibration dataset to determine an amount and/or concentration of NT-proBNP. The meter displays or communicates an assay result to the user.

Example 2

Figure 17:
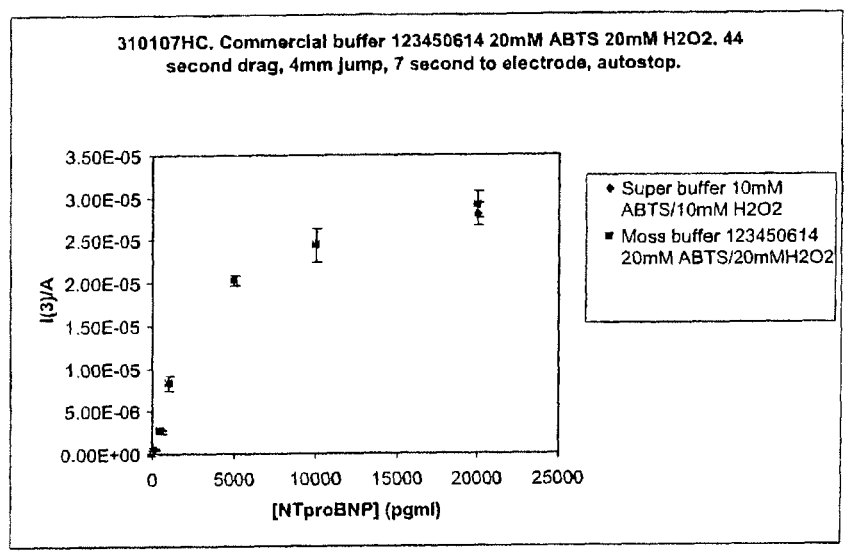
FIG. 17 shows a typical dose response curve for NT-proBNP concentrations 0-20,000 pg/ml.

Extension/Linearization of the Measurable NT-proBNP Range—Two Point Electrochemical Measurements to Extend the Dynamic Range Electrochemical measurements can be made using a single time point of HRP turnover time. A typical dose response curve for concentrations of 0-20,000 pg/ml NT-proBNP in the liquid sample is shown in FIG. 17. The performance of the electrochemical NT-proBNP assay may be optimised by extending the measurable range and linearising the response at the higher NT-proBNP concentrations. To achieve this we identified whether the plateau effect was a reagent, electrochemical or combined reagent and electrochemical limitation.

Figure 18:
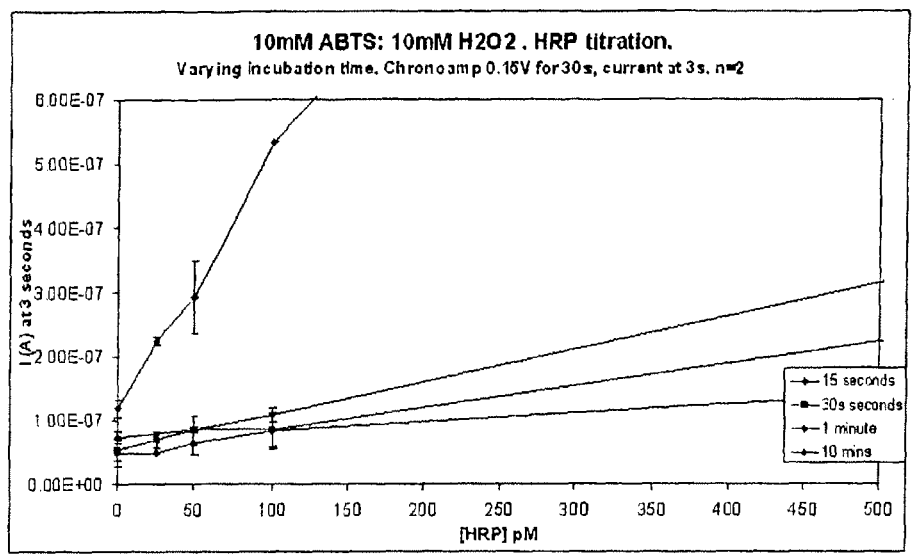
FIG. 18 illustrates summary HRP titration data at turnover times of 10 mins, 1 min, 30 sec and 15 seconds.

Within the current electrochemical measurement of NT-proBNP, effectively we are measuring the concentration of HRP; this is illustrated in FIG. 18. Therefore dose response curves of NT-proBNP are effectively current vs. HRP concentration.

The ability to measure the HRP concentration electrochemically via the mediator ABTS provides the flexibility to tune the immunoassay response. Typically, once the particles were moved out of the blood and dragged to the electrode, captured HRP was allowed to react for a 1 minute turnover period (incubation time). No potential was applied to the electrode until after the 1 minute HRP turnover period, the subsequent potential applied was used to reduce the oxidised ABTS generated by the HRP.

To investigate the limitation of a 1 minute HRP turnover period, HRP titrations were performed to investigate the HRP turnover time on the sensitivity, linearity and range of the response. In these experiments the HRP was homogeneously distributed within the channel and not concentrated in the vicinity of the electrode when placed on the electrode via the magnetic particles.

The linear range of the HRP is seen to vary with turnover time. A 10 minute turnover time results in an approximately linear range up to 5000 pM HRP; a 1 minute turnover time results in an approximately linear range up to 20,000 pM HRP; a 30 second turnover time results in a approximately linear range of 50,000 pM HRP; a 15 second turnover time results in an approximately linear range of 80,000 pM HRP.

The effect of HRP turnover time is summarised in FIG. 18. There is a trade off between increased linearity of the HRP response and sensitivity, as the HRP range (pM) is increased the HRP measurement becomes less sensitive e.g. 10 minutes—limit of detection (LOD) at least 25 pM; 1 min—LOD 50-100 pM; 30 secs 100 pM; 15 secs LOD 100 pM.

From the titration data we conclude that we can significantly increase the measurable HRP concentration (pM) range and the linear component.

Figure 19:
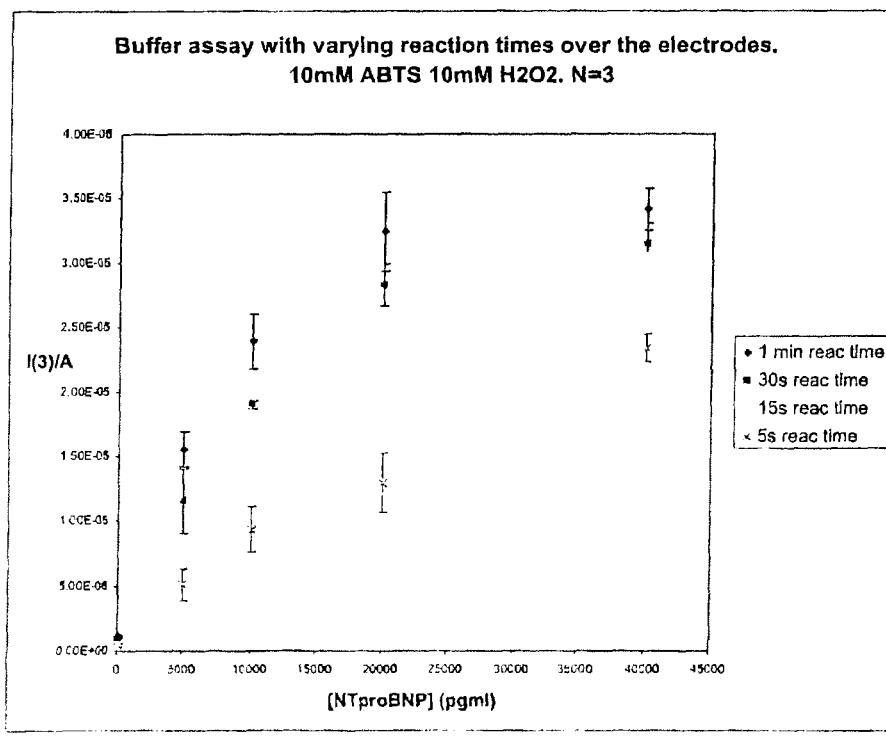
FIG. 19 illustrates NT-proBNP electrochemical assay results for 0, 5000, 10,000, 20,000 and 40,000 pg/ml NT-proBNP with HRP turnover times of 1 min, 30, 15 and 5 seconds.

Experiments were performed to test this hypothesis, the summary results are shown in FIG. 19.

The application of reduced HRP turnover times has a significant effect upon extending and linearising the NT-proBNP response. This represents a significant optimisation for the electrochemical measurement of NT-proBNP.

It is desirable to be able to measure NT-proBNP concentrations over a 50-20,000 pg/ml range. This is a dynamic range for an immunoassay to measure. It would also be desirable to distinguish a doubling in NT-proBNP concentration. It would also be desirable to linearise the electrochemical response over the higher NT-proBNP concentrations.

Figure 20:
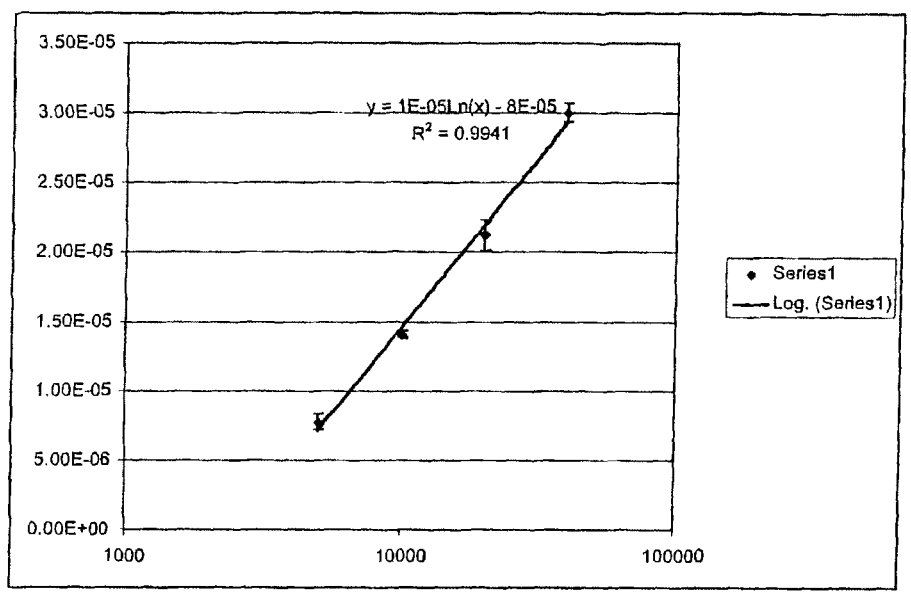
FIG. 20 illustrates a semi-log plot of NT-proBNP electrochemical assay results at a 15 sec turnover time.

For example, a 15 second turnover time allows the measurement of up 40,000 pg/ml NT-proBNP and easily allows the ability to measure the doubling of 5000 to 10000 to 20000 to 40000 pg/ml. This result demonstrates how the assay can be tuned for optimum performance. For example if the 15 sec measurement is plotted on a semi log curve a good linear response is observed as shown in FIG. 20 (x-axis shows NT-proBNP concentration).

This result provides a good model system to understand the complex interplay between many parameters. A two point electrochemical measurement can be made to measure the desired range with optimum performance, for example a 15 second measurement to capture the high NT-proBNP concentrations as shown and then a second measurement (e.g. 1, 2, 3 minutes) to measure the low NT-proBNP concentrations resulting in 2 calibrations curves for maximum sensitivity and performance.

Further HRP titration experiments were performed to investigate the relationship between increased HRP turnover time and increased HRP LOD. A clear trend was observed. The LOD and the associated slope of the response changes as a function of HRP turnover time. Specifically LOD of 10 pM are observed for the 10, 7 and 5 min HRP turnover time whilst 25 pM is observed for 3 mins and a 100 pM LOD for a 1 minute HRP turnover time. Significant increases in performance could be observed using a prolonged HRP time period for measurement of lower NT-proBNP concentrations compared with the previously used 1 minute turnover time. For example a secondary time point measurement after 5 minutes HRP turnover would result in changing the HRP LOD from 100 pM to 10 pM (×10 difference).

Two point HRP titrations experiments were performed. Identical titration responses were observed whether a single HRP concentration is measured in a single or dual time point manner, depletion of the generated oxidised ABTS over a 3 second period does not affect the signal obtained with the second time point measurement (300 sec). Shorter measurement times of the oxidised ABTS (<300 secs) may allow multiple time points to be measured.

Other embodiments are within the scope of the following claims.

What is claimed is:
1. A method comprising:
   depositing a first mixture comprising an antibody-linked enzyme and an antibody-magnetic particle conjugate in a dry state in a reagent control zone of a microfluidic device;
   introducing a liquid sample including an analyte to the reagent control zone in a channel portion of the microfluidic device through an inlet, wherein the analyte is capable of binding the antibody in the antibody-linked enzyme and the antibody in the antibody-magnetic particle conjugate;

contacting the liquid sample containing the analyte with the first mixture to rehydrate the first mixture and form a second mixture, the second mixture including the analyte, the antibody-linked enzyme and the antibody-magnetic particle conjugate at the reagent control zone;

causing the analyte to form an analyte complex with the antibody-linked enzyme and the antibody in the antibody-magnetic particle conjugate such that the complex may be moved under the influence of a magnetic field;

rupturing a fluid reservoir containing a second liquid, the second liquid containing a substrate of the enzyme and introducing the second liquid through a first path to flow toward the reagent control zone;

acquiring a sensor reading from the released second liquid which represents a baseline response as the second liquid passes over a measurement electrode on the way to the reagent control zone;

forming an analyte complex: second liquid interface between the second liquid and the analyte complex at a junction in the reagent control zone;

driving a portion of the second liquid along a second path to an overflow zone, wherein the second liquid encounters a set of electrodes having immobilized thereon a predetermined amount of enzyme, the enzyme being the same enzyme in the antibody-linked enzyme of the first mixture;

reacting the second liquid with the immobilized enzyme to obtain a high control response;

moving the analyte complex across the interface under the influence of a magnetic field;

locating the complex over a measurement electrode;

acquiring a measurement response in the form of an enzyme control signal due to conversion of substrate in the second liquid by the enzyme at a detection zone, the detection zone in proximity of the measurement electrode;

modulating the measurement response according to signals acquired for baseline response and high control response values; and using the reagent enzyme control signal to validate or adjust the assay result.

2. A method according to claim 1, further comprising forming the analyte complex: second liquid interface by flowing the second liquid toward the junction and displacing gas of an analyte complex: gas interface with the second liquid.

3. A method according to claim 1, wherein detecting the enzyme control signal takes place prior to formation of the analyte complex: second liquid interface.

4. A method according to claim 1, wherein detecting the enzyme control signal occurs at a location upstream of the junction with respect to the direction of flow of the second liquid.

5. A method according to claim 1, wherein detecting the enzyme control signal occurs at a location downstream of the junction with respect to the direction of flow of the second liquid.

6. A method according to claim 1, wherein detection of the enzyme control signal occurs in the second liquid after formation of the first liquid: second liquid interface.

7. A method according to claim 1, further comprising comparing the detected enzyme control signal against a reference value.

8. A method according to claim 1, wherein the enzyme is a horse radish peroxidase and the substrate is 2,2'-azino-bis(3-ethylbenzthiazoline-6-sulphonic acid (ABTS), and wherein the second liquid contains hydrogen peroxide.

9. A method according to claim 1, further comprising detecting a substrate control signal in a substrate control zone prior to forming the analyte complex:second liquid interface.

10. The method according to claim 9, further comprising validating or adjusting the assay result based on the substrate control signal.

11. The method according to claim 1, wherein depositing the enzyme is performed simultaneously as providing the enzyme for contacting with the sample in the reagent control zone.

12. The method according to claim 1, further comprising validating an assay when the enzyme control signal is within a normal range.

13. The method according to claim 1, further comprising voiding an assay when the enzyme control signal is outside a normal range.

14. The method according to claim 1, wherein a second channel portion connects the first channel portion at the junction.

15. The method according to claim 1, wherein the reagent control zone has a main channel height $h_1$, and a channel height $h'_1$ at the junction, wherein $h_1 > h'_1$, and wherein the second channel portion has height $h_2$ at the junction, wherein $h_2 > h_1 > h'_1$, and wherein the ratio of $h'_1 : h_2$ is at least 1:2.

16. The method according to claim 1, wherein the reagent control zone is located at least 20 mm downstream of the junction with respect to direction of flow of the second liquid.

* * * * *